United States Patent
Liu et al.

(10) Patent No.: US 9,216,403 B2
(45) Date of Patent: *Dec. 22, 2015

(54) EPOXY CHEMISTRY DERIVED MATERIALS AS REVERSED-PHASE AND HYDROPHOBIC INTERACTION CHROMATOGRAPHY MEDIA, METHOD FOR THEIR SYNTHESIS AND USE

(71) Applicant: DIONEX CORPORATION, Sunnyvale, CA (US)

(72) Inventors: Xiaodong Liu, Cupertino, CA (US); Liang Cao, Fremont, CA (US); Christopher A. Pohl, Union City, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/841,484

(22) Filed: Mar. 15, 2013

(65) Prior Publication Data

US 2014/0260563 A1    Sep. 18, 2014

(51) Int. Cl.

| | |
|---|---|
| *C07F 7/08* | (2006.01) |
| *B01J 20/22* | (2006.01) |
| *B01J 20/286* | (2006.01) |
| *B01J 20/287* | (2006.01) |
| *B01J 20/32* | (2006.01) |
| *B01D 15/20* | (2006.01) |
| *G01N 30/02* | (2006.01) |

(52) U.S. Cl.
CPC ............. *B01J 20/22* (2013.01); *B01D 15/20* (2013.01); *B01J 20/286* (2013.01); *B01J 20/287* (2013.01); *B01J 20/3257* (2013.01); *B01J 20/3259* (2013.01); *G01N 30/02* (2013.01)

(58) Field of Classification Search
USPC ............................ 568/579; 556/12, 426, 427
See application file for complete search history.

(56) References Cited

U.S. PATENT DOCUMENTS

| | | | |
|---|---|---|---|
| 4,382,124 A | 5/1983 | Meitzner et al. | |
| 5,039,419 A | 8/1991 | Bradshaw et al. | |
| 5,130,343 A | 7/1992 | Frechet et al. | |
| 5,260,094 A | 11/1993 | Giannelis et al. | |
| 5,334,310 A | 8/1994 | Frechet et al. | |
| 5,453,185 A | 9/1995 | Frechet et al. | |
| 5,728,457 A | 3/1998 | Frechet et al. | |
| 5,929,214 A | 7/1999 | Peters et al. | |
| 6,528,167 B2 | 3/2003 | O'Gara | |
| 6,887,384 B1 | 5/2005 | Frechet et al. | |
| 7,074,331 B2 | 7/2006 | Allington et al. | |
| 7,125,488 B2 | 10/2006 | Li | |
| 7,303,671 B2 | 12/2007 | Srinivasan et al. | |
| 7,468,130 B2 | 12/2008 | Liu et al. | |
| 7,557,232 B2* | 7/2009 | Liu et al. ................ | 556/449 |
| 7,767,462 B2 | 8/2010 | Liu et al. | |
| 2005/0178730 A1 | 8/2005 | Li | |
| 2006/0070937 A1 | 4/2006 | Rustamov et al. | |
| 2012/0245301 A1 | 9/2012 | Glad et al. | |

FOREIGN PATENT DOCUMENTS

| | | |
|---|---|---|
| CN | 1092426 | 9/1994 |
| CN | 1374523 | 10/2002 |
| CN | 1376921 | 10/2002 |
| CN | 1381722 | 11/2002 |
| CN | 1561357 | 1/2005 |
| CN | 101306263 | 11/2008 |
| EP | 0172579 B1 | 11/1992 |
| EP | 0355376 A2 | 12/1995 |
| JP | 8310809 | 11/1996 |
| WO | 2008147717 A1 | 12/2008 |
| WO | 2009009188 A2 | 1/2009 |
| WO | 2012112553 | 8/2012 |
| WO | 2013093872 A1 | 6/2013 |

OTHER PUBLICATIONS

Maehr, "A Proposed Hew Convention for Graphic Presentation of Molecular Geometry and Topography," J. Chem. Ed., 62:114-120 (1985).
Ikada et al., "Reaction of Poly(vinyl Alcohol) with Potassium Persulfate and Graft Copolymerization," Journal of Polymer Science, vol. 12, 1829-1839 (1974).
Majors and Przybyciel, "Columns for Reversed-Phase LC Separations in Highly Aqueous Mobile Phases," LC-GC Europe, Dec. 2002.

* cited by examiner

*Primary Examiner* — Sudhakar Katakam
*Assistant Examiner* — Pancham Bakshi
(74) *Attorney, Agent, or Firm* — Jeffry S. Mann

(57) ABSTRACT

This invention provides aqueous-compatible, polar-embedded reversed-phase stationary phase compositions, devices and systems comprising the stationary phases as well as methods of producing these compositions using epoxide ring-opening reactions. Also provided are methods of using the stationary phases of the invention in separations.

24 Claims, 22 Drawing Sheets

EPOXY CHEMISTRY DERIVED MATERIALS AS REVERSED-PHASE AND HYDROPHOBIC INTERACTION CHROMATOGRAPHY MEDIA, METHOD FOR THEIR SYNTHESIS AND USE

FIELD OF THE INVENTION

The epoxy ring-opening reaction is a well-known and versatile approach to introduce various functionalities in organic synthesis. The same synthetic methodology can be applied to modify solid substrates, including inorganic, polymeric, or inorganic/organic hybrid materials that contain epoxy, hydroxyl, and thiol groups, for developing a broad range of novel stationary phases for chromatographic applications.

BACKGROUND OF THE INVENTION

While conventional reversed-phase columns (e.g. C18) are most widely used for small molecule separations, some drawbacks impede their use in certain applications, such as peak tailing of basic molecules at pH7, due to the undesired interactions between the protonated basic molecules and negatively charged underivatized surface silanols (Si—OH) groups. Recent advances in silica synthesis and bonding technology provide solutions to minimize base tailing by using high-purity silica, high surface coverage, and exhaustive end-capping. However, the resulting stationary phases are usually incompatible with highly aqueous mobile phases due to "phase collapse" or "de-wetting."

Polar-embedded reversed-phase materials can improve the peak shape of basic analytes and make resulting columns fully operational in highly aqueous environment. These phases are primarily hydrophobic but have hydrophilic groups incorporated near the silica surface. The commonly used polar groups are amide, sulfonamide, urea, ether and carbamate functionalities. Two approaches have been used to make such materials. The first reported polar-embedded phase was prepared by a two-step surface modification method. In Step One, silica particles were modified with an aminopropyl silane. In Step Two, the surface amino groups were treated with an alkyl acyl chloride to form an amide linkage between the alkyl chain and the silica surface. The main drawback of this approach is that some un-reacted residual amino groups are always present in the final product, resulting in undesirable chromatographic properties for acidic molecules. The second generation of polar-embedded phases was prepared using a one-step surface modification approach: a silane ligand that contained both alkyl chain and embedded polar group was synthesized first before being bonded to silica particles. While this approach yields an "anion-exchange free" surface, the cost for making such special silane ligand is relatively high, and a subsequent end-capping step to minimize the presence of surface silanol groups is often required.

Another approach to obtain "aqueous-compatibility" reversed-phase stationary phases is to end-cap the reversed-phase surface with a hydrophilic end-capping reagent. In this case, two different silane reagents are needed. In addition, the hydrolytic stability of hydrophilic end-capping group is usually inferior to the reversed-phase ligand, resulting in selectivity drift throughout its lifetime.

SUMMARY OF THE INVENTION

This invention relates to a new methodology for making a broad range of novel aqueous-compatible, polar-embedded reverse-phase stationary phases using the epoxide ring-opening reaction. Exemplary stationary phases of the invention contain a reverse-phase ("RP") moiety (e.g. alkyl or aryl) and an ether or thiol ether linkage with hydroxyl group pendent from the RP moiety.

In an exemplary embodiment, the invention provides a composition (e.g., a stationary phase) comprising a moiety covalently bound to a substrate (FIG. 1-FIG. 3). In various embodiments, the compound has a structure according to Formula (I):

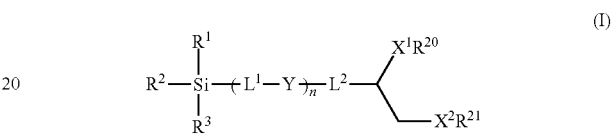

in which n is an integer selected from 0 and 1. In various embodiments, $X^1$ and $X^2$ are independently selected from O and S. In various embodiments at least one of $X^1$ or $X^2$ is O. The moiety $R^{20}$ is selected from the group consisting of H, substituted or unsubstituted phenyl, and linear or branched alkyl optionally substituted with hydroxyl or alkoxy substituted with hydroxy. The symbol $R^{21}$ represents a moiety selected from the group consisting of H, substituted or unsubstituted phenyl, and linear or branched alkyl optionally substituted with hydroxyl or alkoxy substituted with hydroxy. In an exemplary embodiment, $R^{20}$ and $R^{21}$ cannot both be H. In an exemplary embodiment, one but not both of $R^{20}$ and $R^{21}$ is H. In various embodiments, $R^1$, $R^2$ and $R^3$ are selected independently from the group consisting of halogen, $OR^{10}$, $NR^{10}R^{11}$, $OC(O)R^{12}$, $OS(O)_2R^{12}$, substituted or unsubstituted alkyl, substituted or unsubstituted heteroalkyl, substituted or unsubstituted aryl, substituted or unsubstituted heteroaryl, substituted or unsubstituted heterocycloalkyl and a bond to said substrate. Each $R^{10}$ and each $R^{11}$ is selected independently from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl and a bond to a silica substrate with the proviso that, in exemplary embodiments, at least one of $R^1$, $R^2$ and $R^3$ is unsubstituted $C_1$-$C_3$ alkyl or OH. Each $R^{12}$ is selected independently from the group consisting of substituted or unsubstituted alkyl, substituted or unsubstituted heteroalkyl, substituted or unsubstituted aryl, substituted or unsubstituted heteroaryl, and substituted or unsubstituted heterocycloalkyl with the proviso that at least one of $R^1$, $R^2$ and $R^3$ is covalently bound to the substrate. The symbols $L^1$ and $L^2$ represent linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl. Y is an embedded polar group, e.g., O or S.

The invention also provides chromatographic devices, e.g., packings, columns and monoliths, and chromatographic systems incorporating the compositions of the invention. Also provided are methods of making the stationary phases of the invention, methods of using them in chromatographic analyses and purifications.

Additional embodiments, objects and advantages of the present invention are set forth in the detailed description below.

BRIEF DESCRIPTION OF THE DRAWINGS

FIG. 4B shows a scheme for preparing Phase 16, with a neutral hydrophilic layer formed by cross-linking ligands attached to the silica substrate.

DETAILED DESCRIPTION OF EMBODIMENTS

I. Definitions

Figure 1:
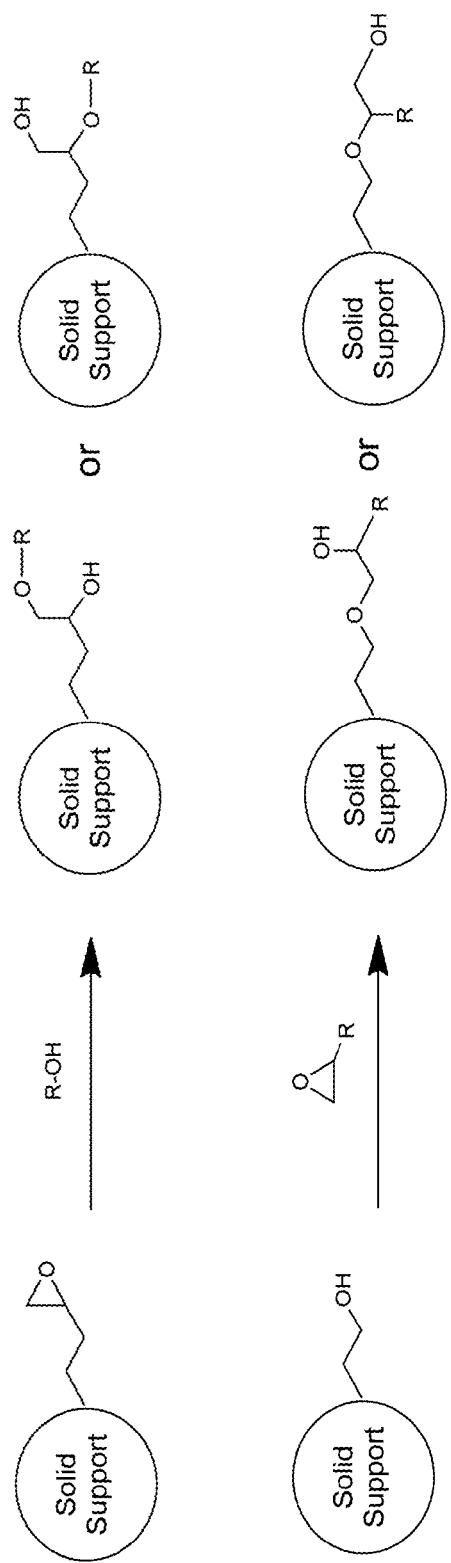
FIG. 1 illustrates the general synthetic route of the epoxy ring-opening reaction.

Where substituent groups are specified by their conventional chemical formulae, written from left to right, they optionally equally encompass the chemically identical substituents, which would result from writing the structure from right to left, e.g., —$CH_2O$— is intended to also recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl (e.g., —$CH_2$—$CH_2$—$CH_3$, —$CH_2$—$CH_2$—$CH_2$—), isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl". The term "alkyl" can also mean "alkylene" or "alkyldiyl" as well as alkylidene in those cases where the alkyl group is a divalent radical.

The term "alkylene" or "alkyldiyl" by itself or as part of another substituent means a divalent radical derived from an alkyl group, as exemplified, but not limited, by —$CH_2CH_2CH_2$—(propylene or propane-1,3-diyl), and further includes those groups described below as "heteroalkylene." Typically, an alkyl (or alkylene) group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl", "lower alkylene" or "lower alkyldiyl" is a shorter chain alkyl, alkylene or alkyldiyl group, generally having about 10 or fewer carbon atoms, about 8 or fewer carbon atoms, about 6 or fewer carbon atoms or about 4 or fewer carbon atoms.

The term "alkylidene" by itself or as part of another substituent means a divalent radical derived from an alkyl group, as exemplified, but not limited, by $CH_3CH_2CH_2$=(propylidene). Typically, an alkylidene group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl" or "lower alkylidene" is a shorter chain alkyl or alkylidene group, generally having about 10 or fewer carbon atoms, about 8 or fewer carbon atoms, about 6 or fewer carbon atoms or about 4 or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, S and B, and wherein the nitrogen and sulfur atoms may optionally be oxidized and the nitrogen heteroatom may optionally be quaternized. The heteroatom(s) O, N, B, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —OS(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—.

The substituents R, R', R" and R''' are preferably independently selected from hydrogen or substituted or unsubstituted (C$_1$-C$_6$)alkyl.

As used herein, the term "silyl group substituent" can be one or more of a variety of groups selected from, but not limited to: substituted or unsubstituted alkyl, substituted or unsubstituted heteroalkyl, substituted or unsubstituted aryl, substituted or unsubstituted heteroaryl, substituted or unsubstituted heterocycloalkyl, acyl, —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —OS(O)$_2$R', —S(O)$_2$NR'R", —NRSO$_2$R', —CN and —NO$_2$. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "non-reactive silyl group substituent" means a "silyl group substituent" that does not react with a substrate of the invention to form a covalent bond between the silyl group substituent and the substrate or, does not behave as a leaving group in a reaction between the ligand (e.g., Formula 1) and the substrate. Exemplary "non-reactive silyl group substituents" include alkyl (e.g., methyl, ethyl, propyl, butyl and other lower alkyl groups) or aryl groups (e.g., phenyl and thiophenyl).

As used herein, the term "reactive silyl group substituent" means a "silyl group substituent" that is capable of reacting with a substrate of the invention to form a covalent bond between the silyl group substituent and the substrate, or which acts as a leaving group in a reaction between the ligand (e.g., Formula 1) and the substrate. Exemplary "reactive silyl group substituents" include those groups that are conventionally defined as leaving groups, such as halogens (e.g., Cl and Br). Other exemplary "reactive silyl group substituents" include alkoxy groups (e.g., methoxy or ethoxy) and primary and secondary amino groups.

As used herein, the term "acyl" describes a substituent containing a carbonyl residue, C(O)R. Exemplary species for R include H, halogen, substituted or unsubstituted alkyl, substituted or unsubstituted hetroalkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S), and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups.

When compounds of the present invention contain relatively basic or acidic functionalities, salts of such compounds are included in the scope of the invention. Salts can be obtained by contacting the neutral form of such compounds with a sufficient amount of the desired acid or base, either neat or in a suitable inert solvent. Examples of salts for relative acidic compounds of the invention include sodium, potassium, calcium, ammonium, organic amino, or magnesium salts, or a similar salts. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science* 1977, 66: 1-19). Certain specific compounds of the present invention contain both basic and acidic functionalities that allow the compounds to be converted into either base or acid addition salts.

When a residue is defined as "O⁻" (e.g. COO⁻), then the formula is meant to optionally include H or a cationic counterion. Preferably, the salt form of the compound is pharmaceutically acceptable.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention. "Compound or a pharmaceutically acceptable salt or solvate of a compound" intends the inclusive meaning of "or", in that a material that is both a salt and a solvate is encompassed.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The terms "average diameter of the particle", "particle size", "average particle size", "median particle size", or any grammatical variation thereof refers to the particle size specification for a substrate (solid-support) of the invention. Particle-sizes are typically provided by the manufacturer. Particle sizes can refer to any type of particle including spherical and irregular-shaped particles.

"Mobile phase" and "eluent" are used interchangeably referring to a liquid that moves dissolved components (e.g., a glycan) of a mixture that is to be separated through a chromatographic column or other separation device. The mobile phase often contains more than one compound and is a mixture of different solvents or a solution of salts, acids, bases, etc.

"Solvent" is a liquid organic compound (e.g., a single compound). An exemplary solvent is at least partially water miscible. In various embodiments, a solvent is fully water miscible. In various embodiments, "solvent" refers to acetonitrile.

II. Introduction

Hydrophobic interaction chromatography (HIC) is a versatile liquid chromatography technique which is useful in protein separations, either as a mode of purification or as an analytical tool. The technique can be used alone or in combination with ion exchange chromatography and gel filtration chromatography. HIC is unique in that proteins bind at high salt concentration and elute at low salt concentration. Elution is accomplished with a reverse salt gradient which is an immediate indication that HIC is being employed. HIC is sometimes referred to as a milder form of reverse phase chromatography (RPC) since HIC utilizes milder binding and elution conditions than RPC and thus typically retains the biological activity of the target protein. HIC requires minimal sample pre-treatment and can thus be used effectively in combination with traditional protein precipitation techniques. Protein binding to HIC media is promoted by moderately high concentrations of anti-chaotropic salts, which also have a stabilizing influence on protein structure. HIC elution is achieved by a linear or stepwise decrease in the concentration of salt in the adsorption buffer with satisfactory recoveries. As a result, HIC is widely used for purifying a variety of biomolecules, such as serum proteins, membrane-bound proteins, nuclear proteins, receptors, cells, and recombinant proteins in research and industrial laboratories.

Figure 2:
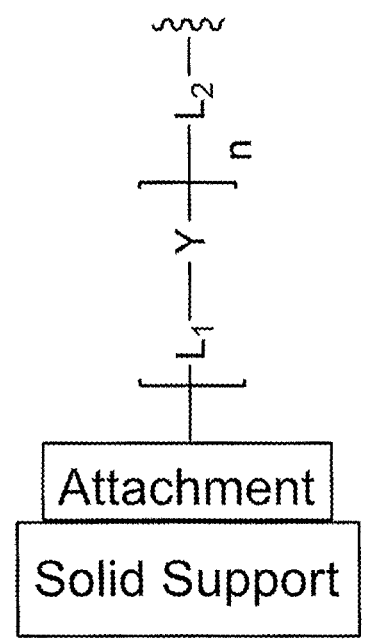
FIG. 2 illustrates the general composition of new stationary phases. Exemplary solid supports include silica, silica/organo hybrid, $TiO_2$, $Al_2O_3$, $ZrO_2$, or a polymer. The solid supports are optionally totally porous, superficially porous, or non-porous. The solid supports can be particulate or monolithic. The attachment between the solid support and the functional layer can be effected through covalent bonding, polymer encapsulation, surface adsorption, or electro-static interaction. $L_1$ and $L_2$ are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl. The index n is an integer from 0 and 1. The symbol Y represents a polar-embedded group, e.g., an ether or thiol ether linkage with a hydroxyl group at the beta position.
Figure 3:
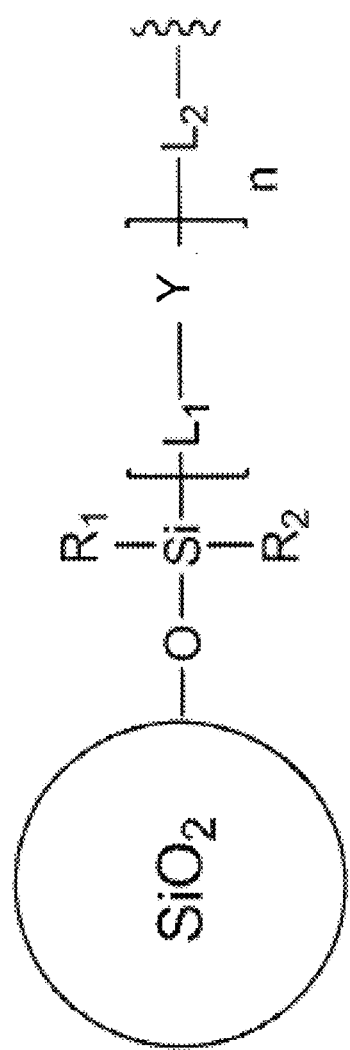
FIG. 3 illustrates the general composition of silica based new stationary phases. $SiO_2$ represents a solid support which is silica, silica/organo hybrid and it can be totally porous, superficially porous, or non-porous; particulate or monolithic. The symbols $R_1$, $R_2$ represent groups independently selected from an oxygen atom that connects to an adjacent silicon atom in the silica substrate, a hydroxyl group, a halogen atom, an alkoxy group (i.e., methoxyl, ethoxyl, etc), an acyl, substituted or unsubstituted alkyl, substituted or unsubstituted heteroalkyl, substituted or unsubstituted aryl, substituted or unsubstituted heteroaryl and substituted or unsubstituted heterocycloalkyl. $L_1$ and $L_2$ are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl. The index n is an integer from 0 and 1. The symbol Y represents a polar-embedded group containing an ether or thiol ether linkage with a hydroxyl group at beta position.

HIC media usually have a hydrophilic surface, a small portion of which is modified with hydrophobic ligands to provide hydrophobic interaction sites. HIC media can be attached to a solid support, e.g., silica gel, cross-linked agarose, or synthetic copolymer materials. Hydrophilic surfaces free of ion exchange properties are important for protein separations by HIC because secondary ion-exchange interactions in addition to primary hydrophobic interactions can adversely affect the separation. While organic polymer based and cross-linked agarose based materials are often used for making HIC media, silica based substrates are desired for their superior mechanical stability, better controlled pore size, high chromatographic efficiency and availability of a broad range of particle sizes (FIG. 2, FIG. 3).

This invention relates to HIC media compositions. The HIC media can be made using epoxide ring-opening reactions (FIG. 1).

III. Stationary Phases

The current invention provides compositions, which are useful as stationary phases or packing materials for a variety of chromatographic applications. Alternatively, the compositions of the invention may be used in other products useful for separation, detection and analysis of compounds, such as membranes, filters and microfluidic devices.

The compositions include a substrate (e.g., silica gel) and a compound, which is covalently bound to the substrate via a silyl group. The compound includes at least one hydrophobic linker as well as an embedded polar group. Exemplary compositions of the invention can generally be described by the following structure, wherein n is either 0 or 1:

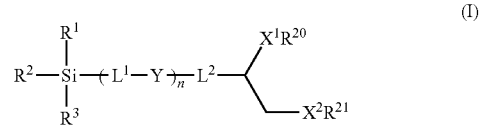

in which n is an integer selected from 0 and 1. In various embodiments, $X^1$ and $X^2$ are independently selected from O and S. In various embodiments at least one of $X^1$ or $X^2$ is O. The moiety $R^{20}$ is selected from the group consisting of H, substituted or unsubstituted phenyl, and linear or branched alkyl optionally substituted with hydroxyl or alkoxy substituted with hydroxy. The symbol $R^{21}$ represents a moiety selected from the group consisting of H, substituted or unsubstituted phenyl, and linear or branched alkyl optionally substituted with hydroxyl or alkoxy substituted with hydroxy. In an exemplary embodiment, $R^{20}$ and $R^{21}$ cannot both be H. In an exemplary embodiment, one but not both of $R^{20}$ and $R^{21}$ is H. In various embodiments, $R^1$, $R^2$ and $R^3$ are selected independently from the group consisting of halogen, $OR^{10}$, $NR^{10}R^{11}$, $OC(O)R^{12}$, $OS(O)_2R^{12}$, substituted or unsubstituted alkyl, substituted or unsubstituted heteroalkyl, substituted or unsubstituted aryl, substituted or unsubstituted heteroaryl, substituted or unsubstituted heterocycloalkyl and a bond to said substrate. Each $R^{10}$ and each $R^{11}$ is selected independently from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl and a bond to a silica gel substrate with the proviso that, in

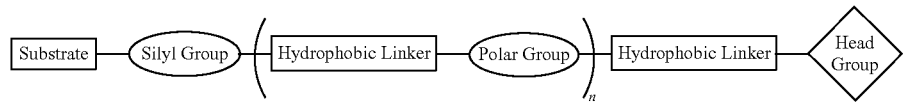

in which the "Head Group" is a polar or non-polar (e.g., hydrophobic head group), e.g., a methyl moiety. Exemplary polar head groups include one or more hydroxyl or alkoxyl moieties. The Silyl Group serves to bind the substrate to the chromatographic functionality. In various embodiments, the index n is 0 or 1. When the index n is 1, the chromatographic functionality includes an embedded polar group. In an exemplary embodiment, the embedded polar group is S or O, See, e.g., FIG. 1-FIG. 3.

In one embodiment, the head group is a diol moiety, alkoxyl or di-alkoxyl moiety. Thus, in a first aspect, the invention provides a composition that includes a compound covalently bound to a substrate, wherein the compound has a structure according to Formula (I), in which n is an integer selected from 0 and 1:

In an exemplary embodiment, the invention provides a composition (e.g., a stationary phase) comprising a moiety covalently bound to a substrate (FIG. 1-FIG. 3). In various embodiments, the compound has a structure according to Formula (I):

exemplary embodiments, at least one of $R^1$, $R^2$ and $R^3$ is unsubstituted $C_1$-$C_3$ alkyl or OH. Each $R^{12}$ is selected independently from the group consisting of substituted or unsubstituted alkyl, substituted or unsubstituted heteroalkyl, substituted or unsubstituted aryl, substituted or unsubstituted heteroaryl, and substituted or unsubstituted heterocycloalkyl with the proviso that at least one of $R^1$, $R^2$ and $R^3$ is covalently bound to the substrate. The symbols $L^1$ and $L^2$ represent linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl. Y is an embedded polar group, e.g., O or S.

In an exemplary embodiment, $R^1$, $R^2$ and $R^3$ are selected independently from the group consisting of $OR^{10}$, $OC(O)R^{12}$, $OS(O)_2R^{12}$, and unsubstituted alkyl, wherein each $R^{10}$ and each $R^{11}$ is selected independently from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl and a bond to a silica gel substrate with the proviso that at least one of $R^1$, $R^2$ and $R^3$ is unsubstituted $C_1$-$C_3$ alkyl or OH. In various embodiments, each $R^{12}$ is selected independently from the group consisting of substituted or unsubstituted alkyl, substituted or unsubstituted heteroalkyl, substituted or unsubstituted aryl, substituted or unsubstituted heteroaryl, and substituted or unsubstituted heterocycloalkyl. Exemplary moieties for $L^1$ include $C_3$ unsubstituted alkyl; and exemplary moieties for $L^2$ include $C_1$-$C_8$ unsubstituted alkyl.

In an exemplary embodiment, $R^{20}$ is selected from the group consisting of H, substituted or unsubstituted phenyl, unsubstituted linear or branched alkyl, and alkyl substituted with substituted or unsubstituted phenyl. The symbol $R^{21}$ represents a moiety selected from the group consisting of H, substituted or unsubstituted phenyl, unsubstituted linear or branched alkyl, and alkyl substituted with substituted or unsubstituted phenyl with the proviso that at least one of $X^1R^{20}$ or $X^2R^{21}$ is OH. In an exemplary embodiment, $R^{20}$ and $R^{21}$ cannot both be H. In an exemplary embodiment, one but not both of $R^{20}$ and $R^{21}$ is H. Exemplary moieties for $R^1$, $R^2$ and $R^3$ are selected independently from the group consisting of $OR^{10}$, $OC(O)R^{12}$, $OS(O)_2R^{12}$, and unsubstituted alkyl. In various embodiments, each $R^{10}$ is selected independently from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl and a bond to a silica gel substrate, with the proviso that at least one of $R^1$, $R^2$ and $R^3$ is unsubstituted $C_1$-$C_3$ alkyl or OH. In an exemplary embodiment, each $R^{12}$ is selected independently from the group consisting of substituted or unsubstituted alkyl, substituted or unsubstituted heteroalkyl, substituted or unsubstituted aryl, substituted or unsubstituted heteroaryl, and substituted or unsubstituted heterocycloalkyl. $L^1$ and $L^2$ are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl. Y is O or S.

In various embodiments, $X^1R^{20}$ is OH.

In various embodiments, $R^{20}$ and $R^{21}$ are independently selected from the group consisting of unsubstituted $C_1$-$C_{10}$ alkyl, methyl substituted with substituted or unsubstituted phenyl, and substituted or unsubstituted phenyl. In an exemplary embodiment, $R^{21}$ is selected from the group consisting of methyl, ethyl, unsubstituted $C_4$ alkyl, unsubstituted $C_{10}$ alkyl, methyl substituted with halogen-substituted phenyl, and unsubstituted phenyl.

In various embodiments, the compound of the invention has the formula:

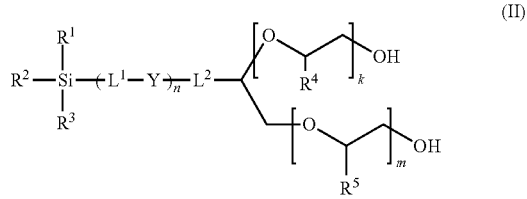

(II)

in which n is an integer selected from 0 and 1; (k+m) is an integer from 1 to 20, e.g., 1 to 10, e.g., 1 to 5, e.g., 1 and 2; $R^4$ is unsubstituted $C_1$-$C_{10}$ alkyl (e.g., methyl, ethyl, or hexadecyl) or phenyl; and $R^5$ is unsubstituted $C_1$-$C_{10}$ alkyl (e.g., methyl, ethyl, or hexadecyl) or phenyl. As will be apparent to those of skill in the art one or more of the hydroxyl moieties can be an SH moiety, an ether or thioether moiety, e.g., $C_6$-$C_{18}$, e.g., $C_8$-$C_{16}$, e.g., $C_8$, $C_9$, $C_{10}$, $C_{11}$, $C_{12}$, $C_{13}$, $C_{14}$, $C_{15}$ or $C_{16}$. In an exemplary embodiment, the alkyl group is not substituted other than at its point of attachment to the remainder of the molecule, i.e., its O- or S-substitution.

In an exemplary embodiment according to either Formula I or Formula II, one, two or three of $R^1$, $R^2$ and $R^3$ is a bond to the substrate or is covalently bound to the substrate. In various embodiments, $R^1$ and $R^2$ are bonds to the substrate or are covalently bound to the substrate, and $R^3$ is unsubstituted $C_1$-$C_3$ alkyl (e.g., methyl) or OH. In an exemplary embodiment, $L^1$ is $C_3$ alkyl.

In various embodiments in which n is 0, $L^2$ is $C_1$-$C_8$ unsubstituted alkyl. In an exemplary embodiment, when n is 0, $L^2$ is $C_8$ unsubstituted alkyl.

In various embodiments, n is 1, and $L^1$ is $C_2$-$C_5$ unsubstituted alkyl, and $L^2$ is $C_1$-$C_3$ unsubstituted alkyl. In an exemplary embodiment, when n is 1, L1 is a $C_3$ unsubstituted alkyl. As will be appreciated by those of skill, the embodiments set forth above are exemplary and, as set forth herein below various parameters of the stationary phases can be varied.

In an exemplary embodiment in which n is 1, $L^1$ is $C_3$ alkyl, Y is O or S, $L^2$ is $CH_2$ and $X^1R^{20}$ and $X^2R^{21}$ are independently selected from OH, SH and ether and thioether moieties. Exemplary alkyl groups for the ether moieties are, e.g., $C_6$-$C_{18}$, e.g., $C_8$-$C_{16}$, e.g., $C_8$, $C_9$, $C_{10}$, $C_{11}$, $C_{12}$, $C_{13}$, $C_{14}$, $C_{15}$ or $C_{16}$. In an exemplary embodiment, the alkyl group is not substituted other than at its point of attachment to the remainder of the molecule, i.e., its O- or S-substitution.

Silyl Group Substituents

In exemplary embodiments according to Formula (I), $R^1$, $R^2$ and $R^3$ are silyl group substituents or a bond to the silica substrate. At least one of $R^1$, $R^2$ and $R^3$ is a covalent bond to, or is covalently bound to, a substrate of the invention. In an exemplary embodiment, one two or three of $R^1$, $R^2$ and $R^3$ is a covalent bond to, or is covalently bound to, the substrate. In various embodiments, the compound of Formula I is a precursor to a stationary phase of the invention and one or more of $R^1$, $R^2$ and $R^3$ is a group reactive with a moiety on the substrate. In an exemplary embodiment, one or more of $R^1$, $R^2$ and $R^3$ is a alkoxyl moiety.

In one example, $R^1$, $R^2$ and $R^3$ are members independently selected from a bond, halogen, $OR^{10}$, $NR^{10}R^{11}$, acyl, $OC(O)R^{12}$, $OS(O)_2R^{12}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein each $R^{10}$ and each $R^{11}$ is a member independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl and a bond to a substrate of the invention (e.g., silica gel). Each $R^{12}$ is a member independently selected from substituted or unsubstituted alkyl, substituted or unsubstituted heteroalkyl, substituted or unsubstituted aryl, substituted or unsubstituted heteroaryl, substituted or unsubstituted heterocycloalkyl.

In another example, at least one of $R^1$, $R^2$ and $R^3$ is a non-reactive silyl group substituent. Exemplary non-reactive silyl group substituents include alkyl groups or aryl groups. In an exemplary embodiment, at least one of $R^1$, $R^2$ and $R^3$ is a member selected from substituted or unsubstituted $C_1$-$C_6$ alkyl (e.g., methyl, ethyl, n-propyl, iso-propyl, n-butyl, iso-butyl and the like). In yet another example, two of $R^1$, $R^2$ and $R^3$ are non-reactive silyl group substituents. For example, two of $R^1$, $R^2$ and $R^3$ are members independently selected from substituted or unsubstituted alkyl, such as substituted or unsubstituted $C_1$-$C_6$ alkyl (e.g., methyl, ethyl, n-propyl, isopropyl, n-butyl, iso-butyl and the like). In an exemplary embodiment, one of $R^1$, $R^2$ and $R^3$ is unsubstituted $C_1$-$C_3$ alkyl or OH. In an exemplary embodiment, one of $R^1$, $R^2$ and $R^3$ is unsubstituted $C_1$-$C_3$ alkyl. In an exemplary embodiment, one of $R^1$, $R^2$ and $R^3$ is methyl. In an exemplary embodiment, one of $R^1$, $R^2$ and $R^3$ is OH. In an exemplary embodiment, two of $R^1$, $R^2$ and $R^3$ are unsubstituted $C_1$-$C_3$ alkyl or OH. In an exemplary embodiment, two of $R^1$, $R^2$ and $R^3$ are unsubstituted $C_1$-$C_3$ alkyl. In an exemplary embodiment, two of $R^1$, $R^2$ and $R^3$ are methyl. In an exemplary embodiment, two of $R^1$, $R^2$ and $R^3$ are OH.

Linkers

In Formula (I), $L^1$ and $L^2$ are linker groups, which in one embodiment, are independently selected from substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment one or both of $L^1$ and $L^2$ is cycloalkyl. In an exemplary embodiment, $L^1$ and $L^2$ are joined by an embedded polar group. In various embodiments, this embedded polar group is designated Y, such as that shown in Formulae Va-Vh. In an exemplary embodiment, this embedded polar moiety is derived from the reaction of glycidyl ether or thioether, and is O or S, respectively. In an exemplary embodiment, the compounds of the invention include at least one hydrophobic linker. In various embodiments, when n is 1, at least one of $L^1$ and $L^2$ in Formula (I) includes a hydrophobic moiety. In various embodiments, when n is 0, $L^2$ includes a hydrophobic moiety. In this context, a "hydrophobic moiety" includes a carbon chain having an exemplary number of carbon atoms in sequence, wherein this number is defined by a lower and an upper limit. With respect to the lower limit the hydrophobic moiety has preferably at least 5, at least 6, at least 7, at least 8, at least 9, at least 10, at least 11, or at least 12 carbon atoms in sequence. In an exemplary embodiment, the hydrophobic moiety has at least 7 carbon atoms in sequence. With respect to the higher limit, the hydrophobic moiety includes preferably not more than about 50 carbon atoms in sequence, not more than about 30 carbon atoms, not more than about 25 carbon atoms, not more than about 20 carbon atoms, or not more than about 15 carbon atoms in sequence. Exemplary ranges for the number of carbon atoms in sequence may be formed between the above described higher and lower limits. In yet another embodiment, the hydrophobic moiety includes more than 50 carbon atoms in sequence.

In various embodiments, at least of $L^1$ and $L^2$ is a carbon chain comprising at least 8 carbon atoms in sequence. In various embodiments, $L^1$ and $L^2$ combined includes at least 8, 9, 10, 11, 12, 13, 14, 15, 16, 17, 18, 19 or at least 20 carbon atoms in sequence.

Within the hydrophobic moiety, at least two of the carbon atoms in sequence are optionally part of a ring (e.g., a 5- or 6-membered ring), wherein the ring is a member selected from aryl, heteroaryl, cycloalkyl and a fused ring system that can include aryl, heteroaryl and cycloalkyl rings. The ring is optionally substituted with a non-polar (hydrophobic) substituent, such as an unsubstituted alkyl group (e.g., methyl, ethyl or propyl group). In an exemplary embodiment, the hydrophobic moiety is sufficiently hydrophobic for the compositions to exhibit reversed phase characteristics.

In an exemplary embodiment, $L^1$ is unsubstituted $C_1$-$C_7$ alkyl. In an exemplary embodiment, $L^1$ is unsubstituted $C_1$-$C_3$ alkyl. In an exemplary embodiment, $L^1$ is unsubstituted $C_4$-$C_7$ alkyl. In an exemplary embodiment, $L^1$ is $C_3$ unsubstituted alkyl.

In an exemplary embodiment, $L^2$ is unsubstituted $C_1$-$C_7$ alkyl. In an exemplary embodiment, $L^2$ is unsubstituted $C_1$-$C_3$ alkyl. In an exemplary embodiment, $L^2$ is unsubstituted $C_4$-$C_7$ alkyl. In an exemplary embodiment, $L^2$ is $C_1$ unsubstituted alkyl. In an exemplary embodiment, $L^2$ includes a hydroxyl or alkoxyl moiety. In various embodiments, the hydroxyl or alkoxyl group is β- to the embedded polar group.

When in Formula (I) n is 1, then the compound of the invention includes an embedded polar group Y. This group can be any suitable group useful to connect the two linker groups $L^1$ and $L^2$. In one embodiment, $L^1$ and $L^2$ are connected through an ether bond or a thioether bond. In an exemplary embodiment, Y is O, or S.

Head Group

The head group can be non-polar or it can be any moiety that includes one, two or more hydroxyl groups. In one embodiment, the polar head group is:

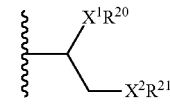

in which $X^1$ is O or S; $X^2$ is O or S; with the proviso that at least one of $X^1$ or $X^2$ is O; $R^{20}$ is selected from the group consisting of H, substituted or unsubstituted phenyl, and linear or branched alkyl optionally substituted with hydroxyl or alkoxy substituted with hydroxy; $R^{21}$ is selected from the group consisting of H, substituted or unsubstituted phenyl, and linear or branched alkyl optionally substituted with hydroxyl or alkoxy substituted with hydroxy. In an exemplary embodiment, $R^{20}$ and $R^{21}$ cannot both be H. In an exemplary embodiment, one but not both of $R^{20}$ and $R^{21}$ is H. In an exemplary embodiment, one or more of $R^{20}$ and $R^{21}$ is a $C_{11}$-$C_{30}$ alkyl or substituted alkyl chain. In an exemplary embodiment, this chain includes 16, 17, 18, 19 or 20 carbon atoms in sequence. In various embodiments, one or both of $R^{20}$ and $R^{21}$ is a moiety recognized in the art to be of use in reverse phase and/or HIC chromatography.

In an exemplary embodiment, the polar head group is:

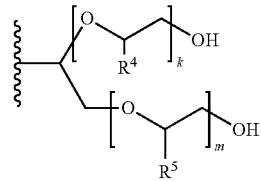

wherein (k+m) is an integer from 1 to 20, e.g., 1 to 10, e.g., 1 to 5, e.g., 1 and 2. $R^4$ is unsubstituted $C_1$-$C_{10}$ alkyl or phenyl and $R^5$ is unsubstituted $C_1$-$C_{10}$ alkyl or phenyl. In an exemplary embodiment, one or more of $R^4$ and $R^5$ is a $C_{11}$-$C_{30}$ alkyl or substituted alkyl chain. In an exemplary embodiment, this chain includes 16, 17, 18, 19 or 20 carbon atoms in sequence. In various embodiments, one or both of $R^4$ and $R^5$ is a moiety recognized in the art to be of use in reverse phase and/or HIC chromatography.

Substrate

The substrate of the invention can be any material (e.g., particles) useful as a stationary phase/packing material for chromatography including porous and non-porous solids.

The substrate or solid support of the chromatographic medium of the invention can be any material (e.g., particles) useful as a chromatographic medium/packing material for chromatography including porous and non-porous solids.

In various embodiments, the solid support is selected from particulates or monoliths. Exemplary particles include silica particles, silica/organo hybrid particles, core-shell particles, $TiO_2$ particles, $ZrO_2$ particles, and $Al_2O_3$ particles.

Exemplary substrates include cross-linked and non-crosslinked polymers. Other substrates include silica-based (e.g., silicon oxide), titanium-based (e.g., titanium oxide), germanium-based (e.g., germanium oxide), zirconium-based (e.g., zirconium oxide) and aluminum-based (e.g., aluminum oxide), carbonized materials and metals.

The solid support may be formed from any synthetic resin material. Exemplary synthetic polymer ion-exchange resins include poly(phenol-formaldehyde), poly(acrylic acid), poly (methacrylic acid), polynitriles, amine-epichlorohydrin copolymers, graft polymers of styrene on polyethylene or polypropylene, poly(2-chloromethyl-1,3-butadiene), poly (vinylaromatic) resins such as those derived from styrene, α-methylstyrene, chlorostyrene, chloromethylstyrene, vinyltoluene, vinylnaphthalene or vinylpyridine, corresponding esters of acrylic acid and methacrylic acid, and similar unsaturated monomers, mono-vinylidene monomers including the monovinylidine ring-containing nitrogen heterocyclic compounds, and any copolymers of the above resins. Additional examples include glycidyl acrylate-based and glycidyl methacrylate-based materials (e.g., 2-glycidyloxyethyl methacrylate, vinylbenzyl glycidyl ether, 2-(4-vinylbenzyloxy)ethyl glycidyl ether) as well as those derived from vinylbenzyl chlorides, vinylbenzyl alcohols, 2-(4-vinylbenzyloxy)ethanol, polyacrylamides, polyvinylalcohols, polyvinylformamides.

Any of the above materials can optionally be co-polymerized with monomers incorporating ionic or ionizable, reverse-phase and/or HILIC functionalities.

In one embodiment, the support comprises cross-linked polymers or copolymers. An exemplary copolymer is styrene-divinylbenzene copolymer (e.g., PS-DVB). In one example, the styrene-divinylbenzene copolymer contains between about 2% to about 100% divinylbenzene monomer by weight. In another example, the styrene-divinylbenzene copolymer contains between about 25% to about 80% divinylbenzene monomer by weight. The copolymer can be prepared, for example, according to the method of Ikada et al., *Journal of Polymer Science*, Vol. 12, 1829-1839 (1974) or as described in U.S. Pat. No. 4,382,124 to Meitzner, et al.

In one example, the solid support includes a silica, alumina, zirconia, or titania-polymeric resin hybrid material. Exemplary silica-organic hybrids are described in U.S. Pat. No. 6,528,167 and U.S. Patent Application Publication 2006/0070937 (application Ser. No. 11/240,695), the disclosures of which are incorporated herein by reference for all purposes.

In one embodiment, a solid support of use in the present invention is formed by well known suspension polymerization techniques. In this example, the particles are typically derived from a monomer mixture, which is insoluble in the solvents with which they will be contacted. Exemplary substrates are formed by heating and stirring a suspension of monomers in a suitable solvent in the presence of a suitable emulsifying agent. Alternatively, the polymerization may be carried out by a suspension, bulk or solution process followed by grinding the resin to a desired size by mechanical means (e.g., ball mills, rod mills or the like).

The solid support can be of any form, including particulates (e.g., spherical, essentially spherical; e.g., resin beads), chips, chunks, blocks, monoliths and the like. When the substrate is in particulate form, the particles (e.g., irregular-shaped or bead-shaped, e.g., essentially spherical) have a median particle size (i.e., diameter). In one example, the median particle size of the substrate (e.g., spherical silica gel) is between about 0.1 (e.g., silica micro-spheres) and about 10,000 μm (microns). In one example, the median particle size of the substrate is between about 1 and about 5000 microns, between about 1 and about 1000 microns, between about 1 and about 500 microns, between about 1 and about 400 microns, between about 1 and about 300 microns, between about 1 and about 200 microns or between about 1 and about 100 microns. In yet another example, the median particle size of the substrate is between about 1 and about 80 microns, between about 1 and about 70 microns, between about 1 and about 60 microns, between about 1 and about 50 microns, between about 1 and about 40 microns, between about 1 and about 30 microns, between about 1 and about 20 microns or between about 1 and about 10 microns. In other example, the median particle size of the substrate particles is between about 10 and about 100 microns, between about 10 and about 80 microns, between about 40 and about 200 microns, between about 40 and about 100 microns, between about 40 and about 80 microns, between about 60 and about 200 microns, between about 60 and about 100 microns, between about 70 and about 200 microns, between about 80 and about 200 microns, between about 100 and about 200 microns, between about 200 and about 600 microns, between about 200 and about 500 microns or between about 200 and about 400 microns.

In an exemplary embodiment, the solid support is a particle of about 1.5 μm to about 20 μm, e.g., from about 1.9 μm to about 3 μm. In various embodiments, the solid support is about 1.9 μm. In various embodiments, the solid support is about 3 μm.

Generally, substrate particles useful in any packed bed chromatographic application (e.g., LC, HPLC or ultra-pressure chromatography) are suitable for use in the chromatographic media of the invention.

In various examples, the support is in particulate form, and multiple support particles are disposed in a packed bed. For example, a plastic or metal column is packed with the support particles. In an exemplary embodiment, the medium of the invention is composed of two or more chromatographic media of the invention, or a medium of the invention and an art-recognized medium. For example, one chromatographic medium is a medium of the invention and the second medium consists of particles with an ion exchange binding site. In various embodiments, the chromatographic medium is mixed with a second chromatographic medium having RP or HILIC binding sites. As will be appreciated multiple chromatographic media, each with a different binding site, are combinable with the chromatographic medium of the invention.

In various examples, the solid support particles are essentially "homodisperse" or essentially "homodisperse", which indicates that the particle size of the majority of the particles (e.g., 80, 90 or 95% of the particles) does not vary substantially (e.g., not more than 50%) below or above the median particle size (M). In an exemplary monodisperse substrate particle population, 90% of the particles have an average particle size of between about 0.5 times M and about 1.5 times M. In an exemplary embodiment, such a particle has a size from about 1.9 μm to about 3 μm. In various embodiments, such a particle is about 1.9 or about 3 μm.

In another example, the substrate is an inorganic or organic monolith. In one example the solid support includes a silica monolith. In another example, the solid support includes an alumina monolith. In yet another example, the solid support includes a zirconia monolith. In a further example, the solid support includes a titania monolith. Exemplary monolithic materials based on organic compositions and methods of preparing such materials are described in U.S. Pat. Nos. 5,130,343; 5,929,214; 5,728,457; 5,260,094; 6,887,384; 5,334,310; 7,303,671; 5,453,185 and 7,074,331.

An exemplary solid support of use in the present invention is assembled by functionalizing a particle with the desired binding site by reaction between moieties of complementary reactivity on the moiety bearing the binding site and the solid support.

In an exemplary embodiment, the substrate is silica gel. Suitable silica gels include non-porous and/or porous silica particles of different pore sizes, preferably from 20 Å to 3000 Å and more preferably, from 50 Å to 5000 Å, from 60 Å to 2000 Å; and of different particle sizes, such as from 0.2 µm to 1000 µm, or from 0.1 µm to 10,000 µm, or from 1 µm to 50 µm. The surface area range of the silica gel can range from 0.1-1,000 m²/g.

In an exemplary embodiment, the stationary phase of the invention include a silica substrate with a particle size from about 1 to about 25 micron in diameter. In various embodiments, the stationary phase of the invention includes a silica substrate with pores from about 100-2000 Å. In various embodiments, the stationary phase of the invention includes a silica substrate with a surface area of from about 1 to about 500 m²/g.

Exemplary Compositions of the Invention

In various exemplary embodiments, in Formula (I), n is 0 and $L^2$ is straight or branched substituted or unsubstituted alkyl. In an exemplary embodiment, $L^2$ is alkyl-substituted- or unsubstituted-$C_5$-$C_{30}$ alkyl. In an exemplary embodiment, $L^2$ is unsubstituted $C_6$-$C_{25}$ alkyl. In an exemplary embodiment, $L^2$ is unsubstituted $C_6$-$C_{20}$ alkyl. In an exemplary embodiment $L^2$ is $C_6$, $C_7$, $C_8$, $C_9$, $C_{10}$, $C_{11}$, $C_{12}$, $C_{13}$, $C_{14}$ or $C_{15}$ unsubstituted alkyl. An exemplary structure according to this embodiment is provided below:

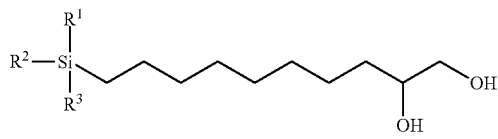

In an exemplary embodiment, at least one of $R^1$, $R^2$ and $R^3$ in Formula (I) is $OR^{10}$ wherein $R^{10}$ represents a bond to the substrate (e.g., silica gel). In an exemplary embodiment, at least two of $R^1$, $R^2$ and $R^3$ in Formula (I) is $OR^{10}$ wherein $R^{10}$ represents a bond to the substrate (e.g., silica gel).

Exemplary compositions of the invention have a structure according to Formula (V):

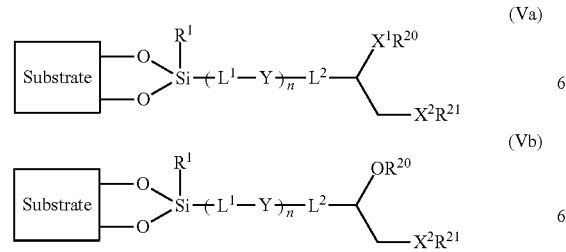

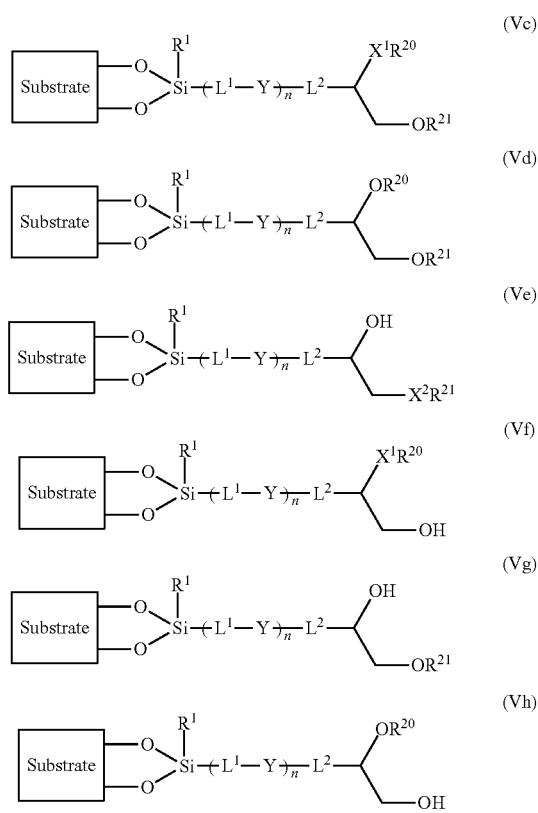

wherein n is an integer selected from 0 and 1 and $R^1$, $R^{20}$, $R^{21}$, $L^1$, $L^2$ and Y as well as the substrate are defined as above for Formula (I).

In one embodiment $R^1$ in Formula (V) is a non-reactive silyl group substituent. In an exemplary embodiment, $R^1$ is a member selected from substituted or unsubstituted alkyl. In one example, $R^1$ is unsubstituted $C_1$-$C_6$ alkyl (e.g., methyl, ethyl, n-propyl, iso-propyl, n-butyl, iso-butyl and the like). In an exemplary embodiment, $R^1$ is methyl. In an exemplary embodiment, $R^1$ is OH.

Exemplary compositions according to Formula (V), when n=0, include:

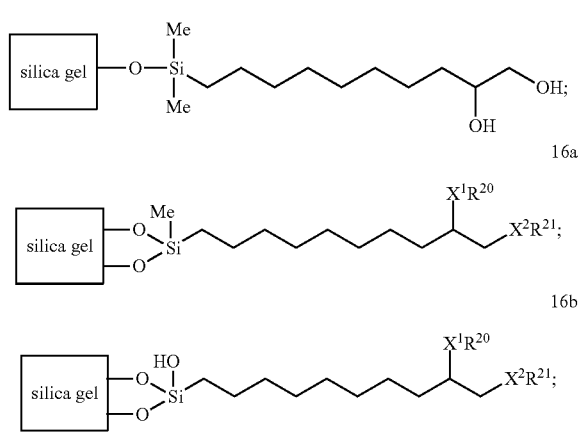

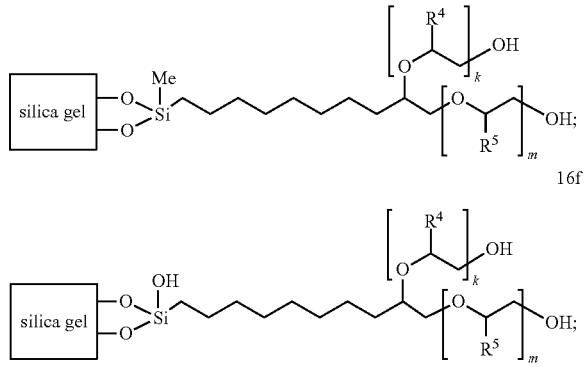

16e

16f

In exemplary embodiments in which n is 1, compositions according to Formula (V) include:

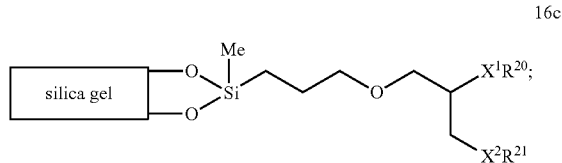

16c

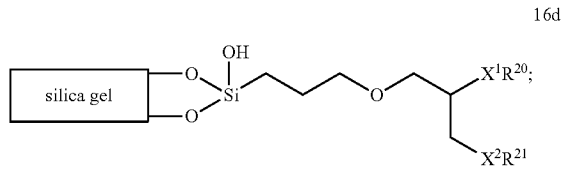

16d

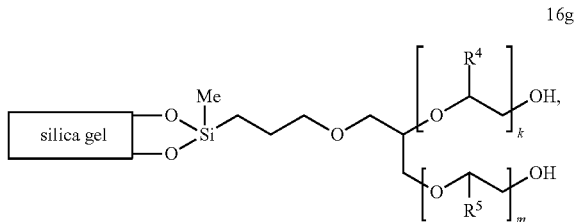

16g

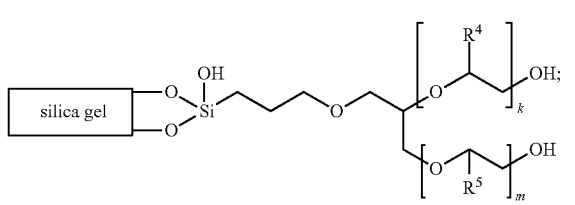

16h

In an exemplary embodiment, $R^{20}$ and $R^{21}$ are selected independently from the group consisting of H, substituted or unsubstituted alkyl, substituted or unsubstituted heteroalkyl, substituted or unsubstituted cycloalkyl, substituted or unsubstituted aryl, substituted or unsubstituted heteroaryl, and substituted or unsubstituted heterocycloalkyl. In an exemplary embodiment, $R^{20}$ and $R^{21}$ cannot both be H. In an exemplary embodiment, one but not both of $R^{20}$ and $R^{21}$ is H. In an exemplary embodiment, $R^{20}$ and $R^{21}$ are selected independently from the group consisting of H, substituted or unsubstituted phenyl, and linear or branched alkyl optionally substituted with hydroxyl or alkoxy substituted with hydroxy. In an exemplary embodiment, $R^{20}$ and $R^{21}$ cannot both be H. In an exemplary embodiment, one but not both of $R^{20}$ and $R^{21}$ is H. In an exemplary embodiment, at least one of $R^{20}$ and $R^{21}$ is H.

In an exemplary embodiment, one or both of $R^{20}$ and $R^{21}$ is a polyhedral oligomeric silsequioxane (POSS) moiety. Examples of POSS moieties, and methods of obtaining same, are known in the art and are described in documents such as PCT Patent Application No. PCT/US2012/025049.

In an exemplary embodiment, $R^4$ is unsubstituted $C_1$-$C_{10}$ alkyl or phenyl. In an exemplary embodiment, $R^5$ is unsubstituted $C_1$-$C_{10}$ alkyl or phenyl. In an exemplary embodiment, $R^4$ is methyl, ethyl, propyl, isopropyl, or phenyl. In an exemplary embodiment, $R^5$ is methyl, ethyl, propyl, isopropyl, or phenyl.

In various embodiments, the compound of the invention is formed by first treating the substrate with the desired ligand, e.g., 1. Following the placement of the ligand on the solid support by covalent bonding, the stationary phase can be used as is or, in exemplary embodiments, the ligand-bound substrate is treated with a small reactive molecule to cap reactive groups on the surface of the substrate. Thus, for example OH moieties on a silica substrate can be left exposed following placement of the ligand on the substrate or they can be capped. An exemplary small molecule capping reagent is a reactive silane, e.g., hexamethyldisilazane.

Selected exemplary compounds are set forth in the figures appended hereto.

The current invention provides embodiments, in which the compositions of the invention are in a container. The container is preferably a chromatography column. Exemplary chromatography columns include metal columns, glass columns and columns made from a polymeric material, such as plastics. Metal columns may be those commonly used for chromatography procedures employing high pressure (e.g., HPLC). Plastic columns may be those commonly employed for preparative chromatography systems. Such polymeric columns are frequently disposable and are often referred to as cartridges.

IIIb. Starting Materials

In various embodiments, the invention provides a compound incorporating a reactive silyl group as well as a precursor moiety (which can be converted into a polar or nonpolar head group). Such compounds have the following general formula:

In one embodiment, the compounds incorporate an epoxide or a hydroxyl moiety as the head group precursor moiety or, in the final product, as the head group itself. Exemplary compounds according to this embodiment have a structure according to Formulae (VIa) and (VIb), wherein n is an integer selected from 0 and 1:

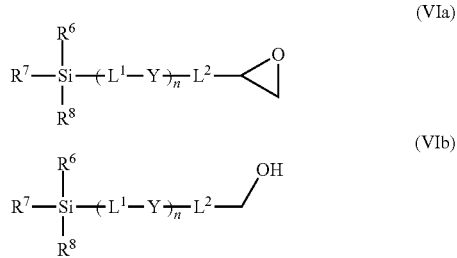

In Formulae (VIa) and (VIb), $R^6$, $R^7$, $R^8$ are defined as for $R^1$, $R^2$, and $R^3$ in Formula I. The index n, $L^1$, $L^2$, and Y are as defined herein for Formula (I). When n is 1, at least one of $L^1$ and $L^2$ in Formulae (VIa) and (VIb), includes a hydrophobic moiety. When n is 0, $L^2$ includes a hydrophobic moiety. In this context, a "hydrophobic moiety" includes a carbon chain having a selected number of carbon atoms in sequence, wherein this number is defined by a lower and an upper limit. With respect to the lower limit the "hydrophobic moiety" has preferably at least 5, at least 6, at least 7, at least 8, at least 9, at least 10, at least 11, or at least 12 carbon atoms in sequence. In an exemplary embodiment, the hydrophobic moiety has at least 7 carbon atoms in sequence. With respect to the higher limit, the "hydrophobic moiety" includes preferably not more than about 50 carbon atoms in sequence, not more than about 30 carbon atoms, not more than about 25 carbon atoms, not more than about 20 carbon atoms, or not more than about 15 carbon atoms in sequence. Exemplary ranges for the number of carbon atoms in sequence may be formed between the above described higher and lower limits. In yet another embodiment, the hydrophobic moiety includes more than 50 carbon atoms in sequence. Within the hydrophobic moiety, at least two of the carbon atoms in sequence are optionally part of a ring (e.g., a 5- or 6-membered ring), wherein the ring is a member selected from aryl, heteroaryl, cycloalkyl and a fused ring system that can include aryl, heteroaryl and cycloalkyl rings. The ring is optionally substituted with a non-polar (hydrophobic) substituent, such as an unsubstituted alkyl group (e.g., methyl, ethyl or propyl group).

In an exemplary embodiment, compounds of the invention represented in the Formulae presented herein (e.g., VIa and VIb) or described in the Examples are useful as precursors to additional compounds of the invention.

In Formula (VI), $R^6$, $R^7$ and $R^8$ are silyl group substituents and together with the Si atom form an activated silyl group. An activated silyl group includes at least one reactive silyl group substituent. A reactive silyl group substituent is capable of reacting with a substrate of the invention to form a covalent bond between the compound and the substrate. Thus, at least one of $R^6$, $R^7$ and $R^8$ is a reactive silyl group substituent. Exemplary reactive silyl group substituents include alkoxy groups, halogens and primary or secondary amino groups.

In one embodiment, $R^6$, $R^7$ and $R^8$ are members independently selected from halogen, $OR^{14}$, $NR^{14}R^{15}$, $OC(O)R^{16}$, $OS(O)_2R^{16}$, acyl, substituted or unsubstituted alkyl, substituted or unsubstituted heteroalkyl, substituted or unsubstituted aryl, substituted or unsubstituted heteroaryl and substituted or unsubstituted heterocycloalkyl. Each $R^{14}$ and each $R^{15}$ is a member independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. Each $R^{16}$ is a member independently selected from substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment, at least one of $R^6$, $R^7$ and $R^8$ is other than OH, unsubstituted alkyl, unsubstituted aryl, unsubstituted heteroaryl and unsubstituted heterocycloalkyl. In an exemplary embodiment, a reactive silyl group substituent is converted to a non-reactive silyl group substituent by "capping". In various embodiments, the silyl group substituent is capped with a reactive silyl reagent, e.g., hexamethyldisilazane.

In one embodiment, one of $R^6$, $R^7$ and $R^8$ is a non-reactive silyl group substituent. In another example, two of $R^6$, $R^7$ and $R^8$ are non-reactive silyl group substituents. Exemplary non-reactive silyl group substituents include alkyl groups or aryl groups. In an exemplary embodiment, one or two of $R^6$, $R^7$ and $R^8$ are members selected from unsubstituted $C_1$-$C_6$ alkyl (e.g., methyl, ethyl, n-propyl, iso-propyl, n-butyl, iso-butyl and the like). In yet another example, two of $R^6$, $R^7$ and $R^8$ are non-reactive silyl group substituents. For example, two of $R^6$, $R^7$ and $R^8$ are members independently selected from substituted or unsubstituted alkyl, such as substituted or unsubstituted $C_1$-$C_6$ alkyl (e.g., methyl, ethyl, n-propyl, iso-propyl, n-butyl, iso-butyl and the like). In an exemplary embodiment, one or two of $R^6$, $R^7$ and $R^8$ are methyl.

IV. Methods

The compositions and compounds of the invention may be synthesized using methods known in the art and those described herein. Exemplary methods are outlined in the Schemes and in the Examples. Variation of those methods may be necessary to synthesize compounds of certain embodiments. Those alternative methods will be apparent to a person of skill in the art. Starting materials and reagents useful for preparing the compositions and compounds of the invention are commercially available or can be prepared using art-recognized methodologies.

Synthesis of Compounds According to Formula (VI) (Starting Materials)

In one embodiment, compounds of Formula (VIa) are prepared using a procedure outlined in Scheme 1, below, in which the integer t is a member selected from 0 to 30, preferably from 2 to 20 and most preferably from 2 to 15. In Scheme 1, the terminal double bond of compound 30 is hydrosilylated using a silane in the presence of a catalyst, such as a platinum (0) catalyst, to give compound 31.

Scheme 1a

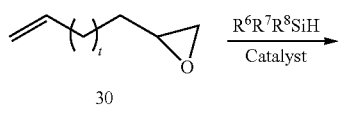

30

-continued

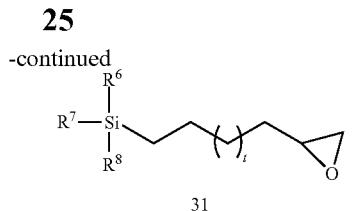

(VIIIb)

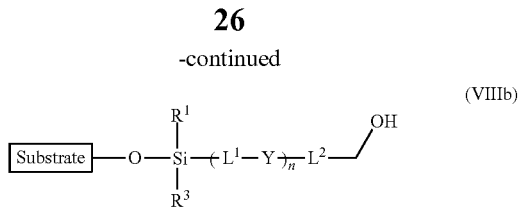

In an exemplary embodiment, a precursor to a ligand of the invention includes a terminal double bond which is oxidized to form an epoxide moiety. Epoxidation reagents are known in the art and include perbenzoic acids, such as meta-chloroperbenzoic acid (m-CPBA). Epoxidation reactions can be performed stereoselectively resulting in chiral products. Chiral epoxides of the invention can be used to synthesize chiral versions of the compositions of the invention useful for chiral chromatography.

Synthesis of Compounds According to Formula (I)

Compounds of Formulae (VIa) and (VIb) can be covalently attached to a substrate (e.g., silica gel) to form a composition of the invention. In one embodiment, a covalent bond between the substrate and the compound is formed through reaction of the substrate with at least one reactive silyl group substituent of the compound. In an exemplary embodiment, the substrate includes reactive functional groups that react with the reactive silyl group substituent to form a covalent bond. Exemplary reactive functional groups of the substrate include silanol and alkoxy silane groups as well as halosilane and aminosilane moieties.

Typically, reaction between a silica substrate and a compound of the invention is effected by heating a mixture of the compound and a slurry of the silica substrate in an inert solvent (e.g., toluene). For example, the mixture is heated to reflux for from about 2 to about 100 hours, preferably from about 10 to about 80 hours, and more preferably from about 10 to about 60 hours. Optionally, a coupling catalyst is added to control the density of the bonded groups on the surface of the substrate as well as the morphology of the resulting phase.

The above described coupling procedure results in intermediate compositions incorporating a polar head group precursor moiety, such as an epoxide or a hydroxy moiety. In one embodiment, the intermediate composition has a structure according to Formulae (VIIa) or (VIIb):

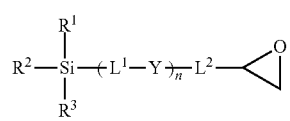

(VIIa)

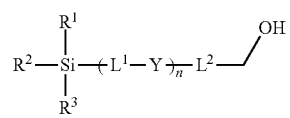

(VIIb)

In one example the intermediate compositions have a structure according to Formulae (VIIIa) and (VIIIb):

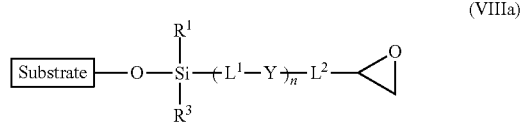

(VIIIa)

The above intermediate compositions of Formulae (VIIa), (VIIb), (VIIIa), and (VIIIb) are useful as stationary phases in chromatography and are within the scope of the current invention.

The intermediate compositions of the invention may be converted to further compositions of the invention, for example those of Formula (I), through conversion of the polar head group precursor to a polar head group, such as a 1,2-diol moiety or —$CH(X^1R^{20})(CH_2X^2R^{21})$. In one embodiment, the epoxide moiety of Formula (VIIa) or Formula (VIIIa) is converted to —$CH(X^1R^{20})(CH_2X^2R^{21})$. It is well within the abilities of a skilled person to carry out such a reaction. For example, acid catalyzed hydrolysis can be carried out by treating the intermediate composition with an aqueous solution containing an organic (e.g., formic acid) or inorganic acid.

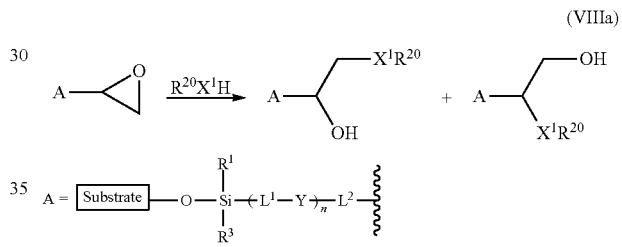

(VIIIa)

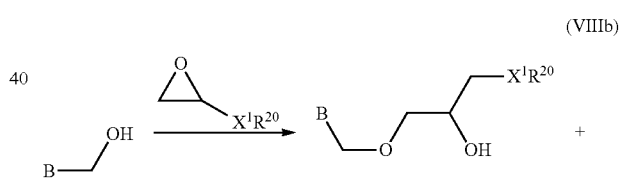

(VIIIb)

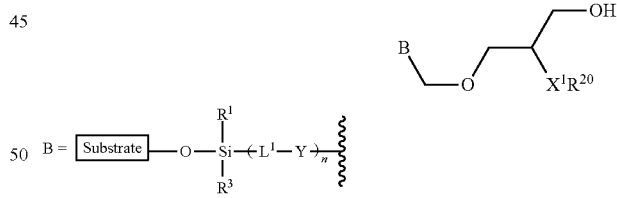

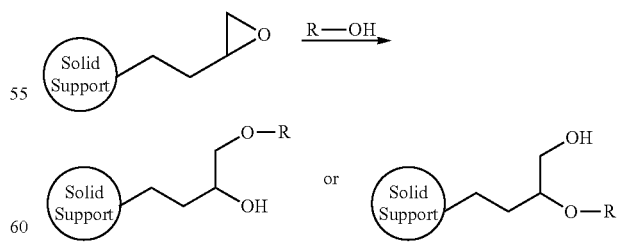

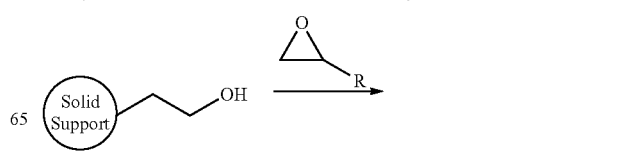

-continued

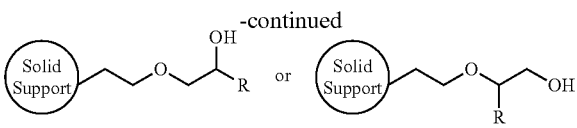

Accordingly, the invention provides methods of making a composition of the invention. In one embodiment, the method includes: (i) contacting a substrate (e.g., silica gel) having a reactive functional group (e.g., a silanol group) with a compound having an epoxide moiety and having a structure according to Formula (VIa):

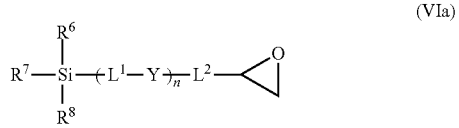

(VIa)

wherein n, $R^6$, $R^7$, $R^8$, $L^1$, $L^2$, $R^4$ and Y are defined herein for Formula (VIa), under conditions sufficient to form a covalent bond between the compound and the substrate through reaction between the reactive functional group of the substrate and at least one of $R^6$, $R^7$ and $R^8$. The method may further include (ii) converting the epoxide moiety into an 1,2-diol moiety, for example, by acid-catalyzed hydrolysis or by opening of the epoxide ring using a nucleophilic reagent as described above. In an exemplary embodiment, at least one of $R^6$, $R^7$ and $R^8$ is halogen or alkoxy (e.g., methoxy or ethoxy).

In an exemplary embodiment, the invention provides a chromatographic stationary support that includes a cross-link formed by components of the compound of Formulae I or II. In an exemplary embodiment, the cross-link results in the formation of a dense, neutral hydrophilic layer covering the substrate. When the substrate is silica, this hydrophilic layer masks the silanol groups on the substrate surface. In various embodiments, the cross-link is formed by reaction between hydroxyl moiety and an epoxide on the same or on different moieties according to Formula I, which are bound to a substrate, and/or a bifunctional reagent. In an exemplary embodiment, either or both the hydroxyl moiety and epoxide moiety are derived from a bifunctional reagent having at least one hydroxyl moiety and at least one epoxide moiety, e.g., glycerol diglycidyl ether, which is contacted with a compound of the invention, e.g., of Formula I or Formula II. As will be apparent to those of skill in the art, the epoxide moiety of the bifunctional reagent can react with a hydroxyl of the ligand bound to the substrate and the hydroxyl of the bifunctional reagent can react with an epoxide on the ligand bound to the substrate and vice versa.

Figure 4A:
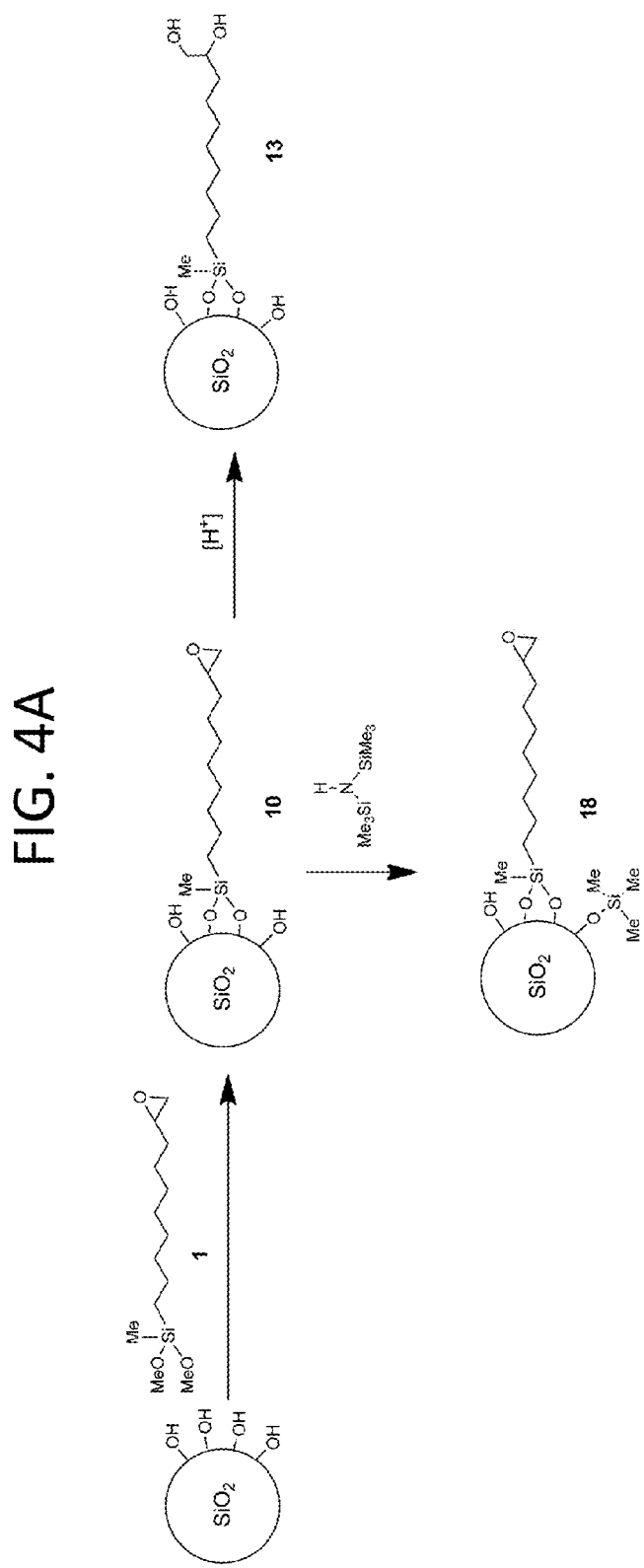
FIG. 4A is a scheme for the preparation of Phases 10, 13 and 18.
Figure 4B:
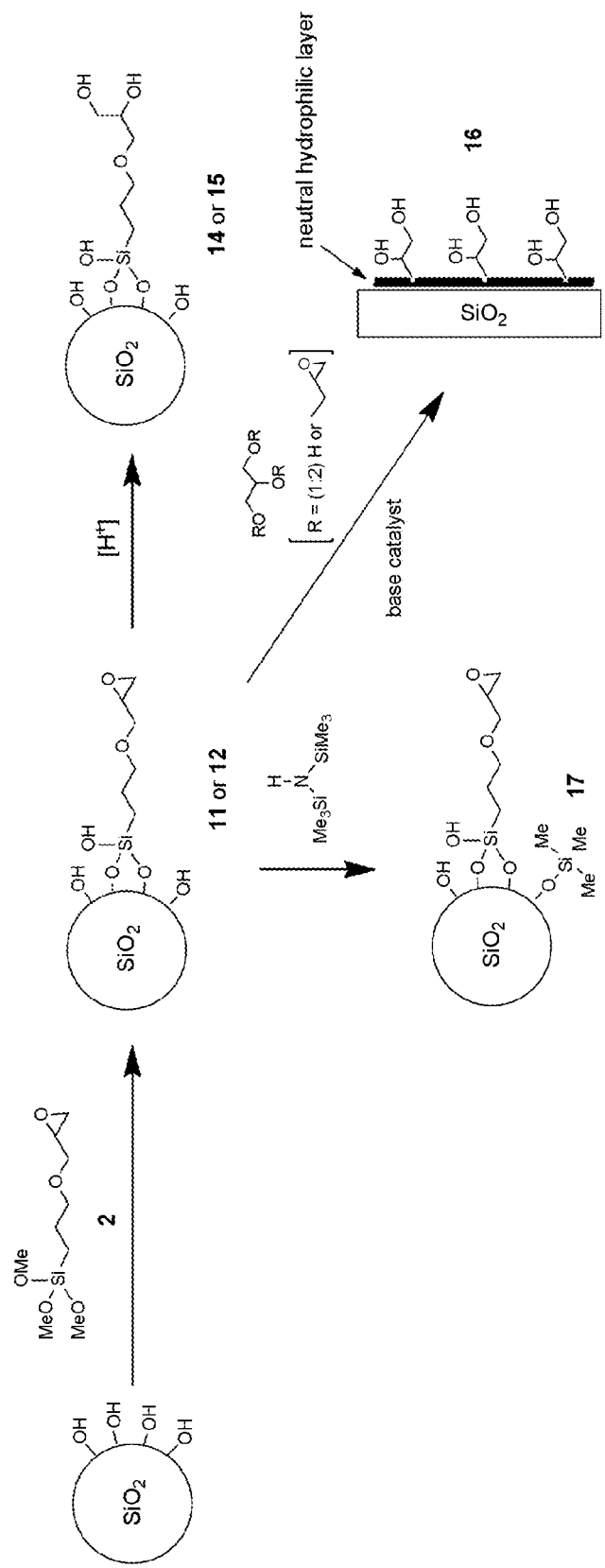
FIG. 4B is a scheme for the preparation of Phases 11, 12, 14, 15, 16 and 17.

In an exemplary embodiment, the invention provides a cross-linked chromatographic stationary support formed by a method comprising: (a) contacting a substrate with a first ligand comprising a first epoxide moiety under conditions appropriate for binding the first ligand to the substrate; (b) contacting the product of step (a) with a bifunctional reagent having at least one hydroxyl moiety and at least a second epoxide moiety under basic conditions, thereby forming a cross-link by reacting said hydroxyl moiety with a member selected from the first epoxide moiety, the second epoxide moiety and a combination thereof; and optionally, (c) contacting the product of step (b) with an epoxide reagent under conditions appropriate to react said epoxide with a hydroxyl moiety on the product of step (b). See, FIG. 4B.

In an exemplary embodiment, only steps (b) and (c) are practiced and the starting material for step (b) is purchased or manufactured prior to forming the cross-linked stationary phase of this embodiment. In an exemplary embodiment, only step (b) is practiced and the product of step (b) is not contacted with the epoxide reagent.

In various embodiments, the reaction of step (b) is performed under basic conditions. The base is an inorganic base (e.g., OH—) or an organic base (e.g., 1,5,7-triazabicyclo [4.4.0]dec-5-ene. In various embodiments, the reaction of step (c) is carried out using boron trifluoride etherate.

Chromatographic Methods

In another embodiment, the invention provides a chromatographic method comprising flowing a mobile phase through a stationary phase comprising a composition of the invention, such as those of Formula (I). In one example, the mobile phase is a liquid. In an exemplary embodiment, the mobile phase includes water. The water content of the mobile phase is preferably between about 0.1% v/v and 60% v/v, more preferably between about 1% and about 20% v/v, even more preferably between about 1% and about 10% v/v and most preferably between about 1% and about 5% v/v.

In another embodiment, the invention provides a method of separating analytes in a liquid sample comprising flowing the liquid sample through a stationary phase comprising a composition of the invention. In an exemplary embodiment, the liquid sample includes water. The water content of the liquid sample is preferably between about 0.1% v/v and 60% v/v, more preferably between about 1% and about 20% v/v, even more preferably between about 1% and about 10% v/v and most preferably between about 1% and about 5% v/v.

V. Devices and Systems

The invention also provides devices and systems incorporating the chromatographic media of the invention. Thus, in an exemplary embodiment, the chromatographic medium is in a flow-through bed suitable for use as a chromatographic device. In an exemplary embodiment, the invention provides a chromatography column packed with the chromatographic medium of the invention.

In an exemplary embodiment, the device is a column packed with a chromatographic medium of the invention. The column hardware in one embodiment of the invention includes rigid tubes to be used as chromatographic columns, with various shapes including cylindrical, conical, rectangular, and polygonal or an assembly of these tubes. The tube may be made from any conventional materials know in the art including metal, glass, silica, plastic or other polymers, more preferably the stainless steel or glass. The inner dimension of this tube can be from micrometers to meters in diameter, thickness, width, or depth. The chromatographic medium may span the entire cross-section area of the tube where the separation of the samples take place by passing through the tube axially or radially (Lee, W-C, et al, "Radial Flow Affinity Chromatography for Trypsin Purification", Protein Purification (book), ACS Symposium Series 427, Chapter 8, American Chemical Society, Washington, D.C., 1990.) depending on the mode of separation, more specifically the axial or direct flow chromatography or the radial flow chromatography. The inner surface of the column may be non-reactive or may be treated to increase adhesion to the surface of chromatographic medium. The tube can incorporate any usable fittings know in the art to connect it with other instruments, more specifically chromatography instruments.

In various embodiments, the invention provides a chromatographic system. In an exemplary embodiment, the system is a high performance liquid chromatography (HPLC) system. Exemplary systems include one or more separation device, which contains a chromatographic medium of the invention. An exemplary system includes one or more separation device in line and in fluidic communication with one or more device for regulating eluent supply to the separation device, e.g., an eluent generator, a pump; one or more detection device, e.g., a mass spectrometric and/or fluorescence detector; and one or more means of introducing a sample on to the separation device, e.g., a sample injection valve.

By way of illustration, exemplary systems for HPLC analysis typically include a chromatographic separation zone using an eluent containing an electrolyte, and an eluent suppression stage, followed by detection, typically performed by mass spectrometer or a fluorescence detector. In the chromatographic separation stage, glycan components of an injected sample are eluted from a separation column.

Eluent is supplied from a source, which can includes a vessel containing premade eluent or it can be generated by an eluent generator. Eluent generators are known in the art. An exemplary eluent generator is disclosed in U.S. Pat. No. 7,767,462.

The invention is further illustrated by the Examples that follow. The Examples are not intended to define or limit the scope of the invention.

EXAMPLES

The following Examples illustrate the synthesis of representative compounds of the invention. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

Example 1

Preparation of Oxirane Functionalized Silica
Preparation of Phase 10 and Phase 18
Dried porous spherical silica particles (20 g of particle size, 5-μm; pore size, 120-Å; surface area, 300 m$^2$/g) were weighed in a 250-mL round bottom flask. A solution of silyl ligand 1 (20 g) in toluene (50 mL) was added to the flask. After carefully dispersing above slurry, the reaction mixture was put under stable refluxing and stirring for 48 hours. The functionalized silica particles were filtered and thoroughly washed with acetone to give Phase 10.

Dried Phase 10 (10 g) was weighed in a 250-mL round bottom flask. hexamethyldisilazane (20 g, e.g., Gelest) and toluene (50 mL) to the flask. After carefully dispersing the slurry, the reaction mixture was put under stable refluxing and stirred for 48 hours. The resulting silica particles were filtered and thoroughly washed with acetone, and finally dried under vacuum at 50° C. for 2 hours to give Phase 18.

Example 2

Preparation of Glycidyl Ether Functionalized Silica
Preparation of Phase 11 and Phase 17
Dried porous spherical silica particles (20 g, particle size, 5-μm; pore size, 120-Å; surface area, 300 m$^2$/g) were weighed in a 250-mL round bottom flask. A solution of silyl ligand 2 (20 g) in toluene (50 mL) was added to the flask. Ligand 2 is commercially available from Gelest (Morrisville, Pa., USA). After carefully dispersing the slurry, the reaction mixture was put under stable refluxing and stirring for 48 h. The functionalized silica particles were filtered and thoroughly washed with acetone to give Phase 11.

Dried Phase 11 (10 g) was weighed in a 250-mL round bottom flask. Hexamethyldisilazane (20 g, e.g., Gelest) and toluene (50 mL) was added to the flask. After carefully dispersing the slurry, the reaction mixture was put under stable refluxing and stirred for 48 hours. The resulting silica particles were filtered and thoroughly washed with acetone, and finally dried under vacuum at 50° C. for 2 hours to give Phase 17.

Example 3

Preparation of Phase 12
Dried porous spherical silica particles (20 g, particle size, 5-μm; pore size, 300-Å; surface area, 100 m$^2$/g) were weighed in a 250-mL round bottom flask. A solution of silyl ligand 2 (10 g) in toluene (50 mL) was added to the flask. After carefully dispersing the slurry, the reaction mixture was put under stable refluxing and stirring for 48 h. The functionalized silica particles were filtered and thoroughly washed with acetone to give Phase 12.

Example 4

Preparation of Hydroxyl Functionalized Silica
Preparation of Phase 13
Phase 10 (10 g) was weighed n a 250-mL plastic bottle with a screw cap. An aqueous solution containing 1% sodium dodecyl sulfate and 0.1% phosphoric acid was added to the bottle. After carefully dispersing the mixture to uniformity, the capped bottle was put on a rotating tumbler at ambient temperature for 20 h. The treated silica particles were filtered and thoroughly washed with acetone to give Phase 13.

Example 5

Preparation of Phase 14
Phase 11 (10 g) was weighed in a 250-mL a plastic bottle with a screw cap. An aqueous solution containing 1% sodium dodecyl sulfate and 0.1% phosphoric acid was added to the bottle. After carefully dispersing the mixture to uniformity, the capped bottle was put on a rotating tumbler at ambient temperature for 20 h. The treated silica particles were filtered and thoroughly washed with acetone to give Phase 14.

Example 6

Preparation of Phase 15
Phase 12 (10 g) was weighed in a 250-mL a plastic bottle with a screw cap. An aqueous solution containing 1% sodium dodecyl sulfate and 0.1% phosphoric acid was added to the bottle. After carefully dispersing the mixture till uniformity, the capped bottle is put on a rotating tumbler at ambient temperature for 20 h. The treated silica particles are filtered and thoroughly washed with acetone to give Phase 15.

Example 7

Figure 5:
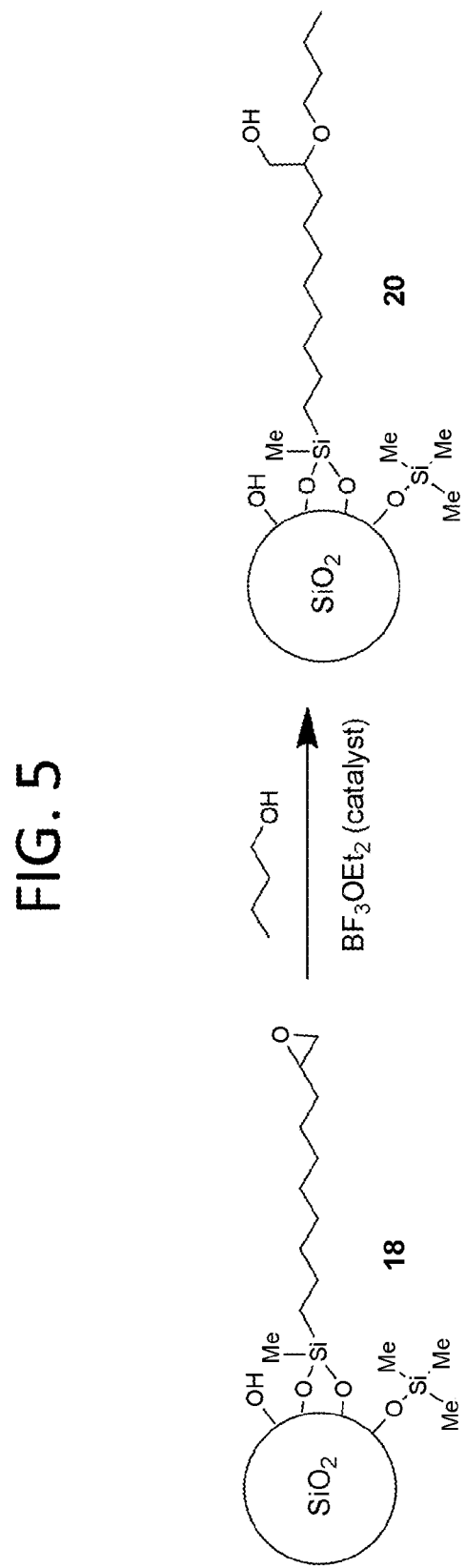
FIG. 5 illustrates the preparation of Phase 20.

Preparation of Aqueous-Compatible Reversed-Phase Materials by Epoxide Ring-Opening Reaction
Preparation of Phase 20 (FIG. 5)
Phase 18 (10 g, vacuum oven dried at 50° C. for 20 h) and toluene (20 mL, anhydrous) were combined in a 40-mL glass vial with a septum cap. After sealing the vial with the cap, the slurry was mixed to uniformity. 1-Butanol (4.0 mL) was added through the septum with a syringe, and the slurry was mixed well. After cooling the mixture with an ice-water bath down to ~4° C., boron trifluoride diethyl etherate (BF$_3$.Et$_2$O) (0.1 mL) was added through the septum with a syringe. The reaction mixture was maintained at ambient temperature with gentle mixing for 30 min. The reaction mixture was filtered followed by washing the filter cake with methanol (50 mL), 0.1% phosphoric acid aqueous solution (200 mL), D.I. water (50 mL) and acetone (100 mL) to give Phase 20.

Example 8

Figure 6:
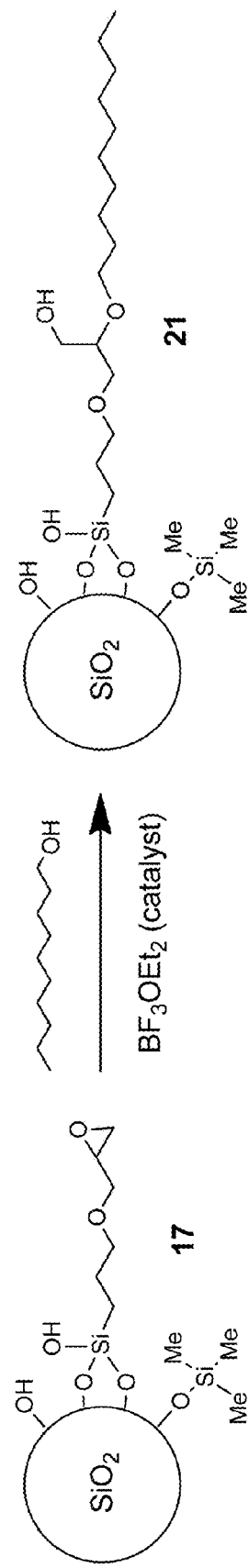
FIG. 6 illustrates the preparation of Phase 21.

Preparation of Phase 21 (FIG. 6)

Phase 17 (4.0 g, vacuum oven dried at 50° C. for 20 h), 4.0 mL of 1-decanol, and 20 mL of toluene (anhydrous) were combined in a 40-mL glass vial with a septum cap. After sealing the vial with the cap, the slurry was mixed to uniformity. The mixture was cooled with an ice-water bath down to ~4° C., and BF$_3$.Et$_2$O (0.1 mL) was added through the septum with a syringe. The reaction mixture was maintained at ambient temperature with gentle mixing for 30 min. The reaction mixture was filtered followed by washing the filter cake with methanol (50 mL), 0.1% phosphoric acid aqueous solution (200 mL), D.I. water (50 mL) and acetone (100 mL) to give Phase 21.

Example 9

Figure 7:
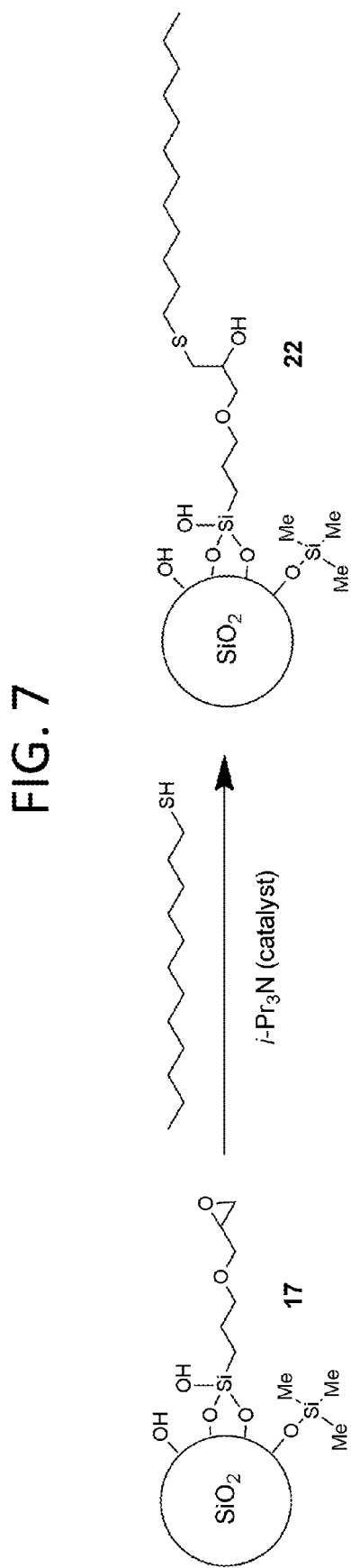
FIG. 7 illustrates the preparation of Phase 22.

Preparation of Phase 22 (FIG. 7)

Phase 17 (4.0 g, vacuum oven dried at 50° C. for 20 h), 4.0 mL of dodecanethiol, and 20 mL of toluene (anhydrous) were combined in a 40-mL glass vial with a septum cap. After sealing the vial with the cap, the slurry was mixed to uniformity. The mixture was cooled with ice-water bath down to ~4° C., then i-Pr$_3$N (1 mL) was added through the septum with a syringe. The reaction mixture was maintained at 80° C. with gentle mixing for 20 h. The reaction mixture was filtered followed by washing the filter cake with methanol (50 mL), 0.1% phosphoric acid aqueous solution (200 mL), D.I. water (50 mL) and acetone (100 mL) to give Phase 22.

Example 10

Figure 8:
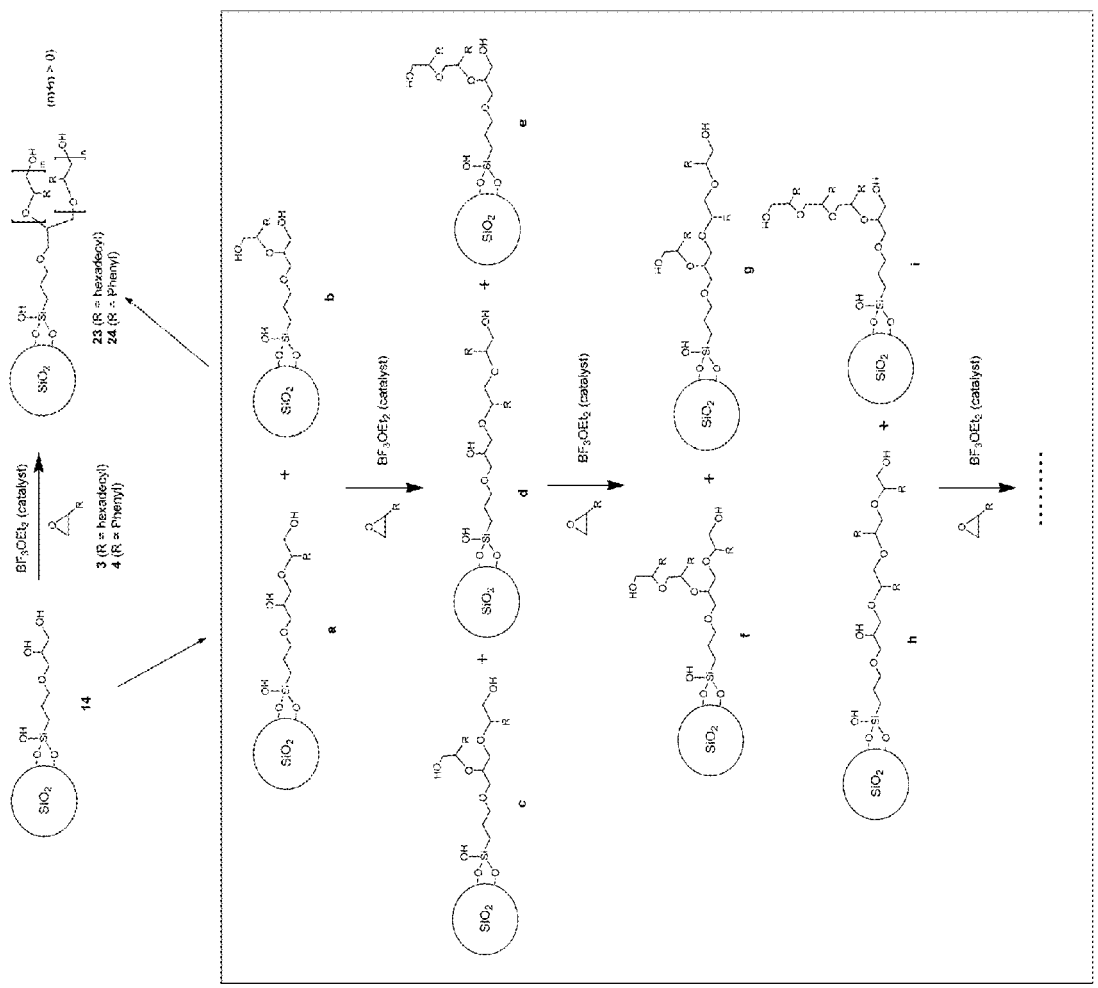
FIG. 8 illustrates the preparation of Phases 23 and 24.

Preparation of Phase 23 (FIG. 8)

Phase 14 (2.0 g, vacuum oven dried at 50° C. for 20 h), 2.0 g of 1,2-epoxyhexadecane (Compound 3), and 20 mL of toluene (anhydrous) were combined in a 40-mL glass vial with a septum cap. After sealing the vial with the cap, the slurry was mixed to uniformity. The mixture was cooled with an ice-water bath down to ~4° C., then BF$_3$.Et$_2$O (0.1 mL) was added through the septum with a syringe. The reaction mixture was maintained at ambient temperature with gentle mixing for 30 min. The reaction mixture was filtered followed by washing the filter cake with methanol (50 mL), D.I. water (50 mL) and acetone (100 mL) to give Phase 23.

Example 11

Preparation of Phase 24 (FIG. 8)

Phase 14 (2.0 g, vacuum oven dried at 50° C. for 20 h) and 20 mL of toluene (anhydrous) were combined in a 40-mL glass vial with a septum cap. After sealing the vial with the cap, the slurry was mixed to uniformity. Styrene oxide (2.0 mL, Compound 4) as added through the septum with a syringe, and the slurry was mixed well. BF$_3$.Et$_2$O (1.0 mL) was added through the septum with a syringe. The reaction mixture was maintained at ambient temperature with gentle mixing for 30 min. The reaction mixture was filtered followed by washing the filter cake with methanol (50 mL), D.I. water (50 mL) and acetone (100 mL) to give Phase 24.

Example 12

Figure 9:
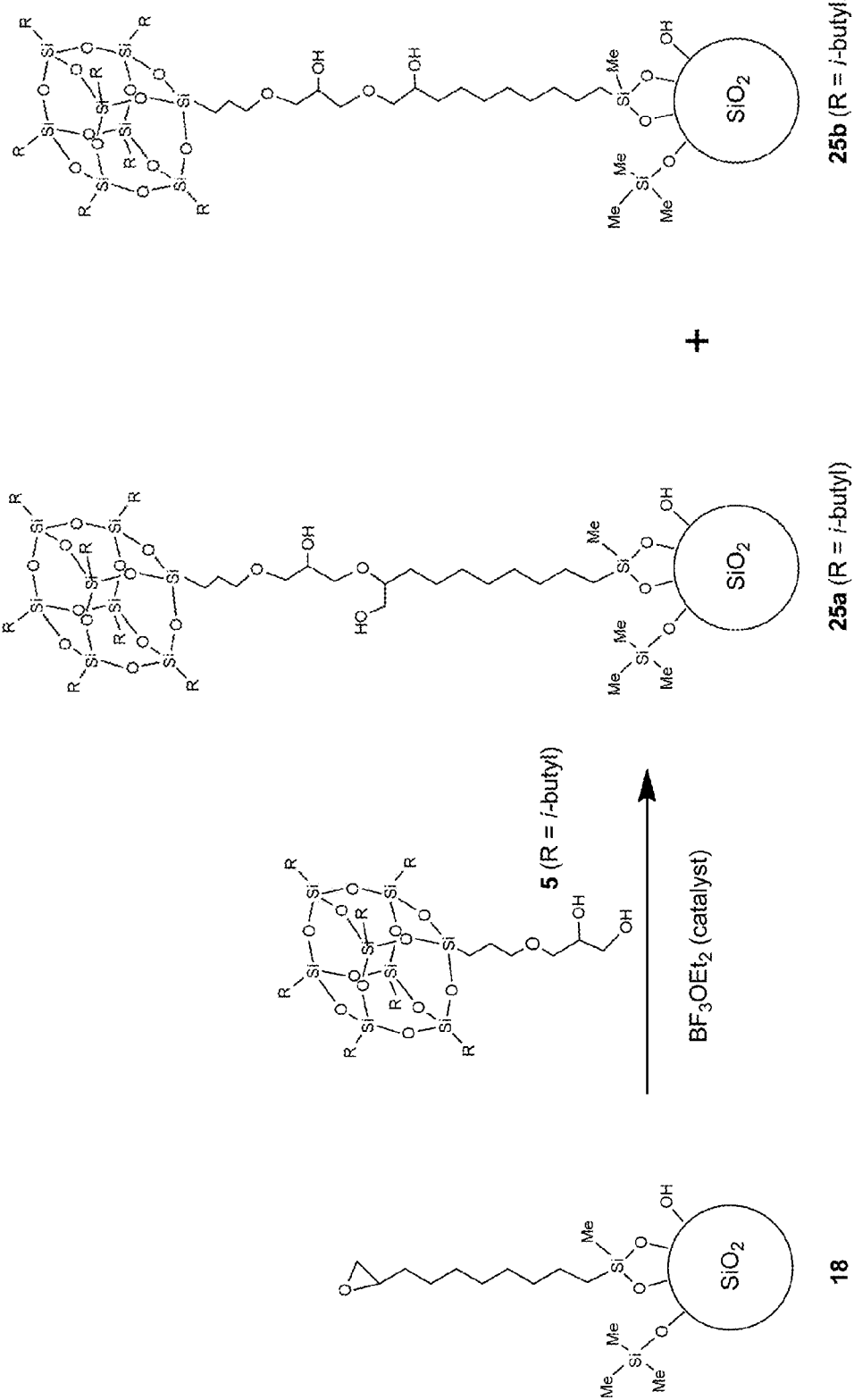
FIG. 9 illustrates the preparation of Phase 25.

Preparation of Phase 25 (FIG. 9)

1-(3-(2,3-Dihydroxypropyl)oxy)propyl-3,5,7,9,11,13,15-isobutylpentacyclo[9.5.1.1.3, 9.15,15.17,13]octasiloxane (1,2-PropaneDiolIsobutyl POSS®, Hybrid Plastics, Cat#: AL0130, CAS[480439-49-4], Compound 5) (2.0 g) was dissolved in 20 mL of toluene (anhydrous) in a 40-mL septa capped glass vial. Phase 18 (2.0 g, vacuum oven dried at 50° C. for 20 h) was added to the vial and the vial was sealed with the cap. The mixture was mixed to uniformity. After cooling the mixture with ice-water bath down to ~4° C., BF$_3$.Et$_2$O (0.1 mL) was added through the septum with a syringe. The reaction mixture was maintained at ambient temperature with gentle mixing for 30 min. The reaction mixture was filtered followed by washing the filter cake with methanol (50 mL), 0.1% phosphoric acid aqueous solution (200 mL), D.I. water (50 mL) and acetone (100 mL) to give Phase 25.

Example 13

Figure 10:
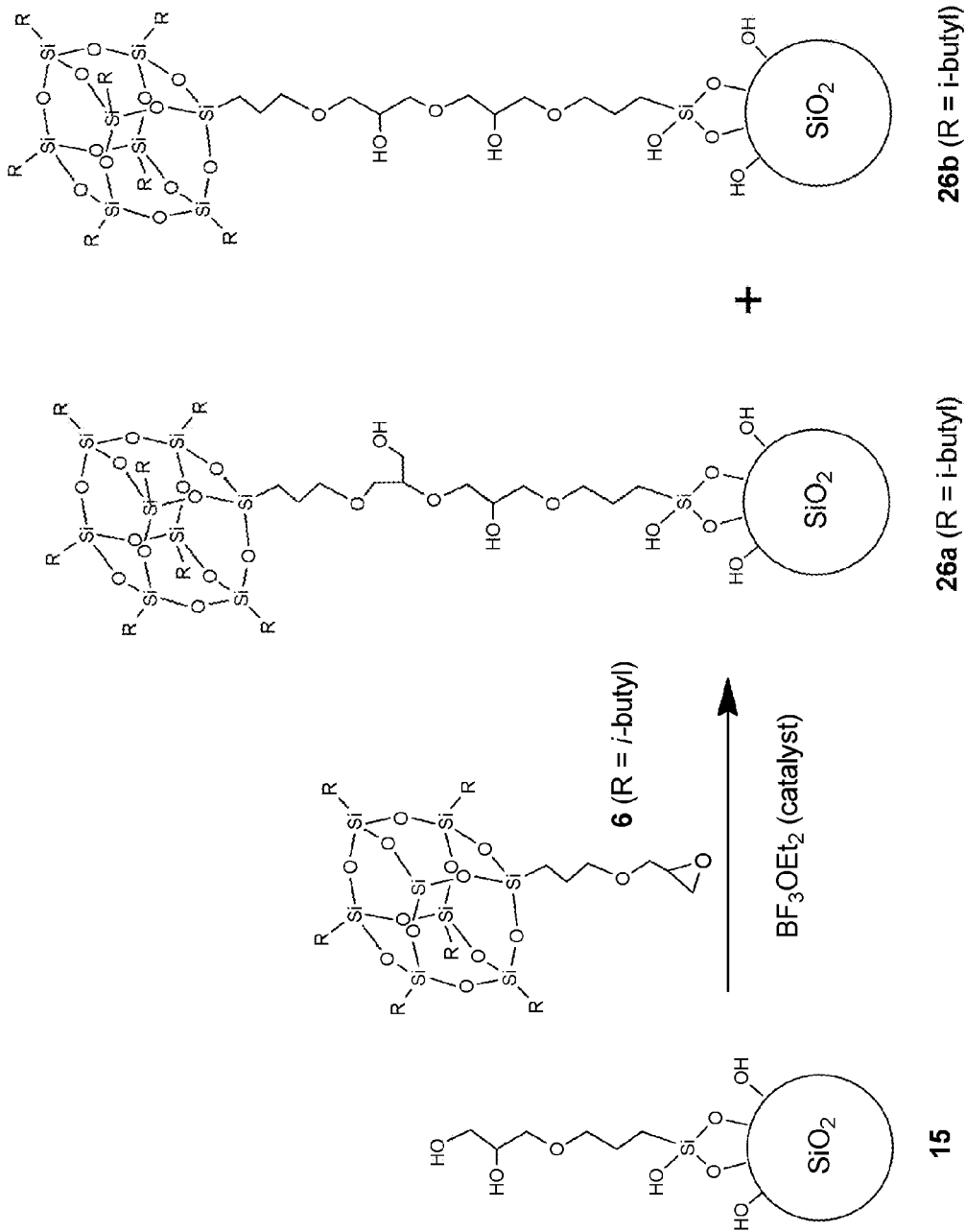
FIG. 10 illustrates the preparation of Phase 26.

Preparation of Phase 26 (FIG. 10)

Glycidylisobutyl POSS® (Hybrid Plastics, Cat#: EP0418, CAS [444315-17-70, Compound 6) (2.0 g) was dissolved in 20 mL of toluene (anhydrous) in a 40-mL septa capped glass vial. Phase 15 (2.0 g, vacuum oven dried at 50° C. for 20 h) was added to the vial and the vial was sealed with the cap. The mixture was mixed to uniformity. After cooling the mixture with ice-water bath down to ~4° C., BF$_3$.Et$_2$O (0.1 mL) was added through the septum with a syringe. The reaction mixture was maintained at ambient temperature with gentle mixing for 30 min. The reaction mixture was filtered followed by washing the filter cake with methanol (50 mL), D.I. water (50 mL) and acetone (100 mL) to give Phase 26.

Example 14

Figure 11:
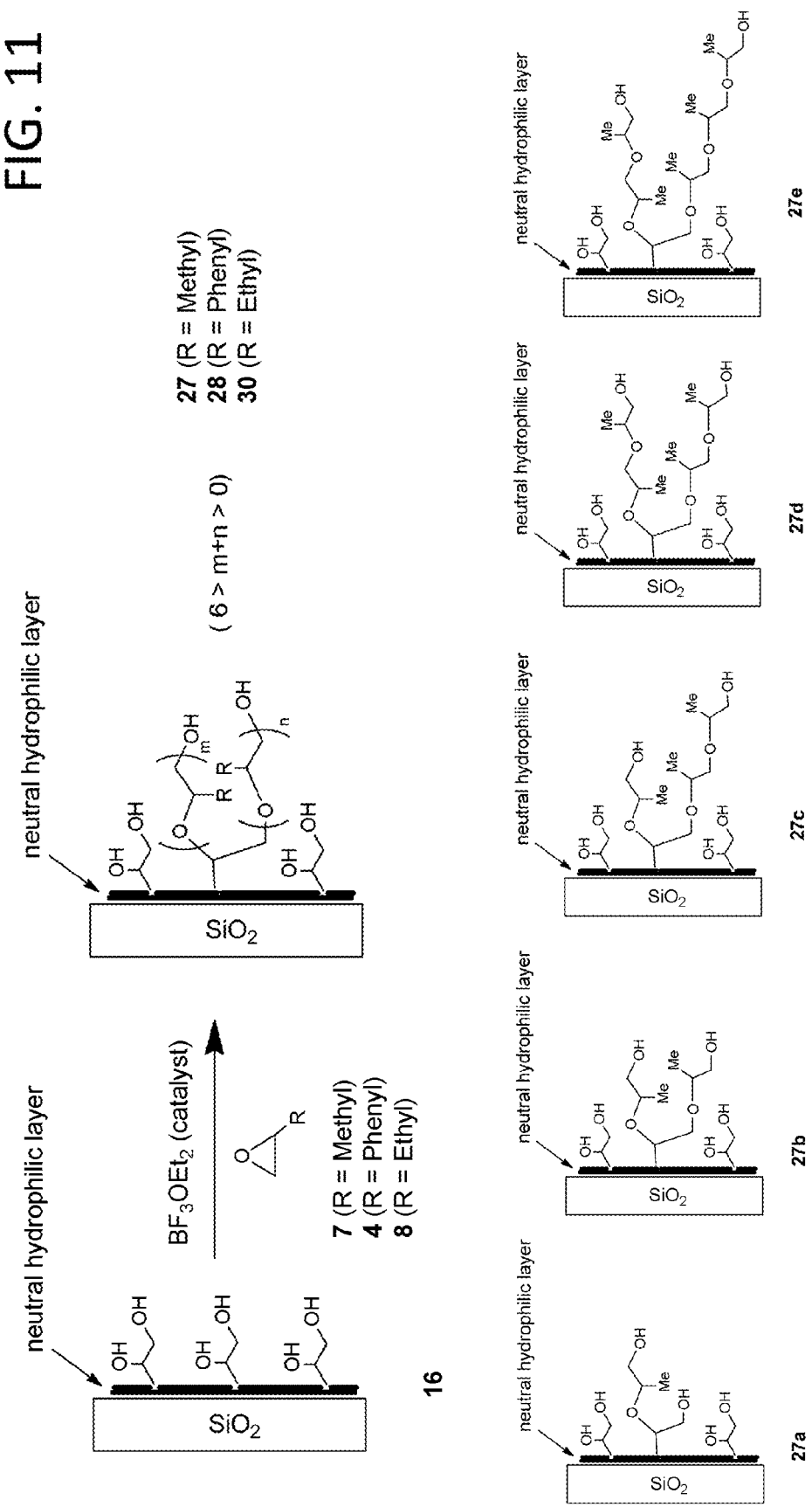
FIG. 11 illustrates the preparation of Phases 27, 28 and 30. Structures of Phases are for illustration purpose only. Epoxide ring-opening reaction may occur at any hydroxyl site.

Preparation of Phase 27 (FIG. 11)

Phase 16 (2.0 g) was combined with 20 mL of toluene (anhydrous) in a 40 mL glass vial with a septum cap. After sealing the vial with the cap, the slurry was mixed to uniformity. Propylene oxide (Compound 7, 0.5 mL) was added through the septum with a syringe, and the slurry was mixed well. After cooling the mixture with ice-water bath down to ~4° C., boron trifluoride diethyl etherate (BF$_3$.Et$_2$O) (0.1 mL) was added through the septum with a syringe. The reaction mixture was maintained at ambient temperature with gentle mixing for 30 min. The reaction mixture was filtered followed by washing the filter cake with methanol (50 mL), D.I. water (50 mL) and acetone (100 mL) to give Phase 27.

Example 15

Preparation of Phase 28 (FIG. 11)

Phase 16 (2.0 g) was combined with 20 mL of toluene (anhydrous) in a 40-mL glass vial with a septa cap. After sealing the vial with the cap, the slurry was mixed well until uniformity. Styrene oxide (Compound 4, 0.5 mL) was added through the septum with a syringe, and the slurry was mixed well. After cooling the mixture with ice-water bath down to ~4° C., 0.1 mL of boron trifluoride diethyl etherate (BF$_3$.Et$_2$O) was added through the septum with a syringe. The reaction mixture was maintained at ambient temperature with gentle mixing for 30 min. The reaction mixture was filtered followed by washing the cake with methanol (50 mL), D.I. water (50 mL) and acetone (100 mL) to give Phase 28.

Example 16

Figure 12:
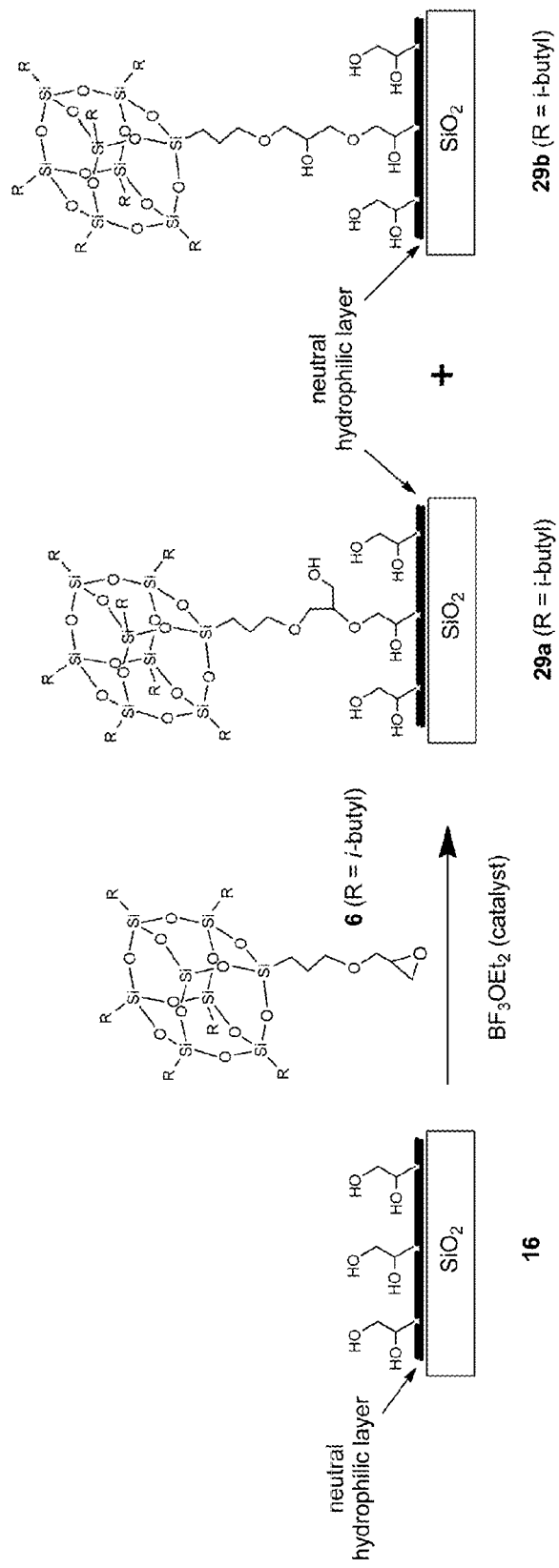
FIG. 12 illustrates the preparation of Phase 29.

Preparation of Phase 29 (FIG. 12)

Glycidylisobutyl POSS® (Hybrid Plastics, Cat#: EP0418, CAS [444315-17-70], and Phase 6 (1.0 g) were combined with 20 mL of toluene (anhydrous) in a 40-mL septa capped glass vial. Dried Phase 16 (2.0 g) was added to the vial and the vial was sealed with the cap. Mix the mixture well until uniform. After cooling the mixture with ice-water bath down to ~4° C., add 0.1 mL of $BF_3.Et_2O$ through the septum with a syringe. Keep the reaction mixture at ambient temperature with gentle mixing for 30 min. The reaction mixture is filtered followed by washing the cake with methanol (50 mL), D.I. water (50 mL) and acetone (100 mL) to give Phase 29.

Example 17

Preparation of Phase 30 (FIG. 11)

Dried Phase 16 (2.0 g) and 20 mL of toluene (anhydrous) were combined in a 40 mL glass vial with a septum cap. After sealing the vial with the cap, the slurry was mixed to uniformity. 1,2-Butylene oxide (Compound 8, 0.5 mL) was added through the septum with a syringe, and the slurry was mixed well. After cooling the mixture with ice-water bath down to ~4° C., add 0.1 mL of boron trifluoride diethyl etherate ($BF_3.Et_2O$) through the septum with a syringe. Keep the reaction mixture at ambient temperature with gentle mixing for 30 min. The reaction mixture is filtered followed by washing the cake with methanol (50 mL), D.I. water (50 mL) and acetone (100 mL) to give Phase 30.

Example 18

Chromatographic Applications

For chromatographic evaluation of Phases 14 and 21-24, the bonded phases were packed into 3.0×50-mm, 3.0×150 mm, 4.6×100-mm stainless steel columns using traditional high-pressure slurry techniques.

Hydrophobicity

Figure 13:
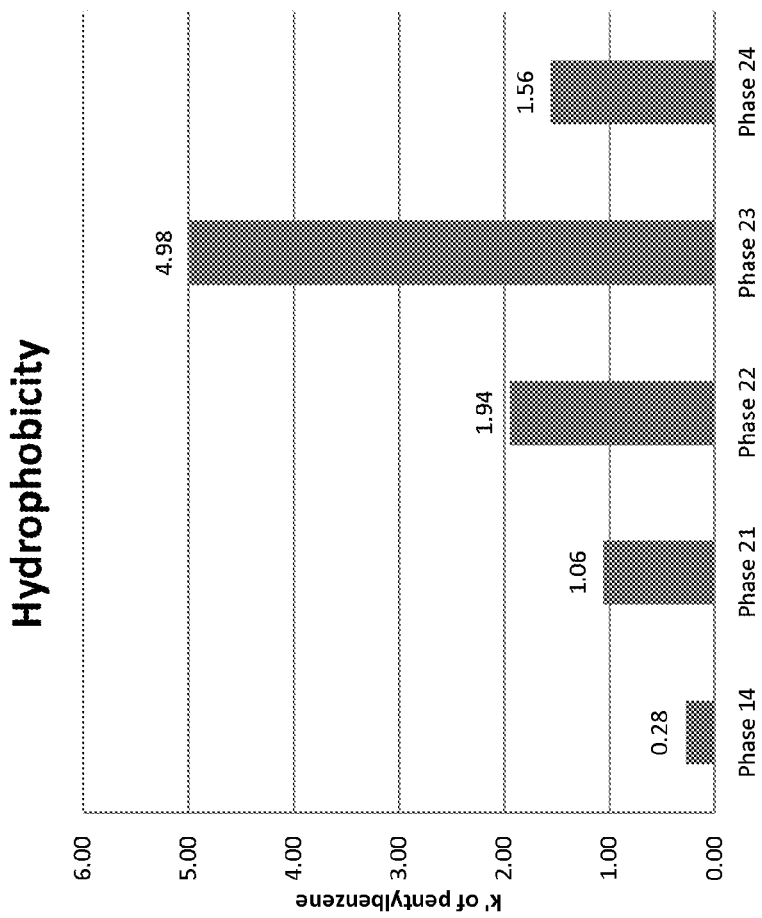
FIG. 13 shows the hydrophobicity comparison of several RP materials prepared by epoxide ring-opening reaction. Due to the incorporation of a hydrophobic moiety into the epoxy or hydroxyl bonded silica, the hydrophobicity of the resulting phase increases significantly. It is clear that hydrophobicity can be adjusted easily by using reagents with various hydrophobic moieties. The conditions for acquisition of the chromatogram were as follows: Column, Phases 14, 21, 22, 23 and 24, 5 μm; Dimensions, 3.0×150 mm; Mobile Phase, MeCN/$H_2O$ v/v 50/50; Temperature, 30° C.; Flow Rate, 0.425 mL/min; Inj. Volume, 3 μL; Detection, UV (254 nm); Sample, 0.5 mg/mL (each); Probe, pentylbenzene (0.5 mg/mL).

Hydrophobicity is an important parameter to characterize a reversed-phase material. Due to the incorporation of a hydrophobic moiety into the epoxy or hydroxyl bonded silica, the hydrophobicity of the resulting phase increases significantly. FIG. 13 shows the hydrophobicity comparison of glycidyl diol bonded phase and several reversed-phase materials derived from it through the epoxy ring-opening reaction. Hydrophobicity of the phases of the invention can be adjusted easily by using reagents with various hydrophobic moieties.

Test condition: column, phases 14 and 21-24, 5-µm, 3×150-mm; mobile phase, acetonitrile/water (50:50 v/v); flow rate, 0.425 mL/min; injection volume, 3 µL; temperature, 30° C.; detection, 254 nm; and test probe, pentylbenzene (0.5 mg/mL).

Example 18A

Steric Selectivity

Figure 14:
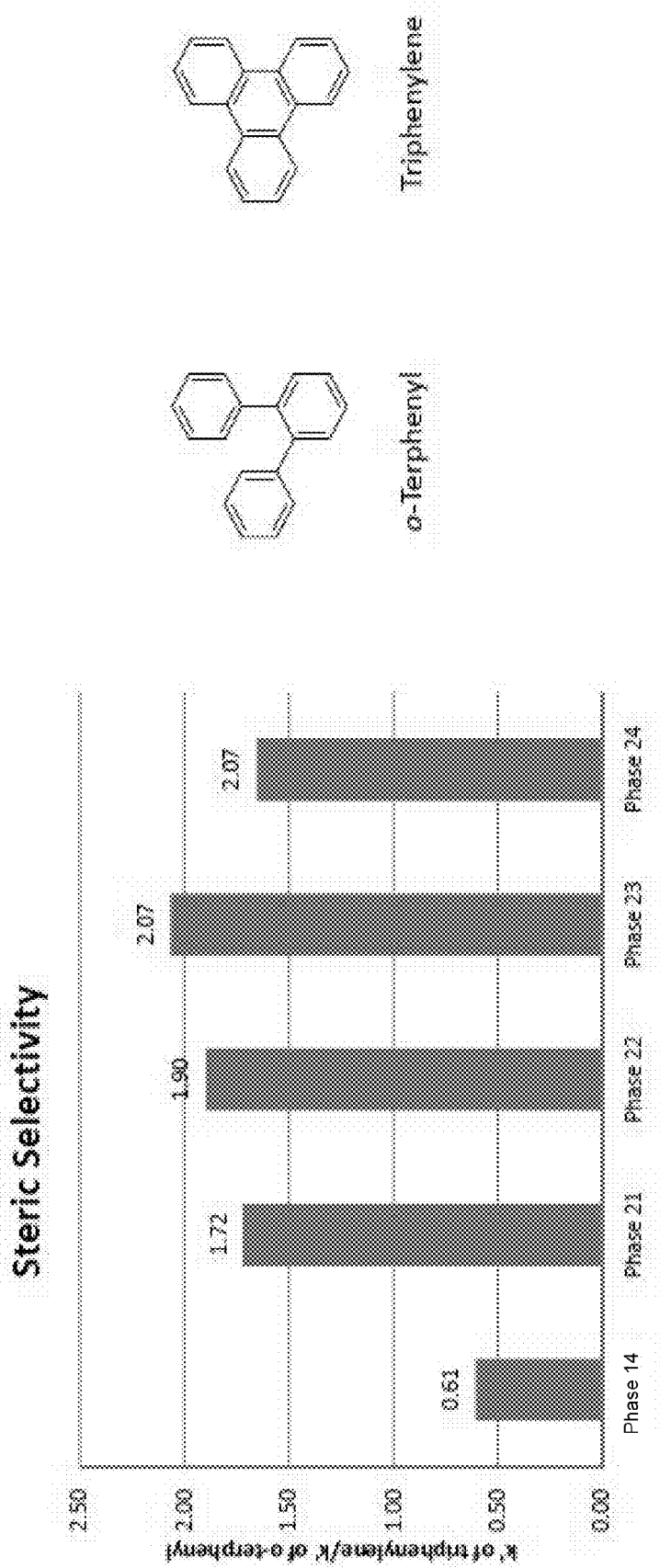
FIG. 14 gives the comparison of steric selectivity of several RP media synthesized by epoxide ring-opening reaction. After incorporation of a hydrophobic moiety into the bonded phase through the epoxide ring-opening reaction, the steric selectivity of resulting bonded phases increase significantly. The chromatogram was acquired under the following conditions: Column, Phases 14, 21, 22, 23 and 24, 5 μm; Dimensions, 3.0×150 mm; Mobile Phase, MeOH/$H_2O$ v/v 80/20; Temperature, 30° C.; Flow Rate, 0.425 mL/min; Inj. Volume, 3 μL; Detection, UV (254 nm); Sample, o-terphenyl and triphenylene (0.1 mg/mL each).

Triphenylene (T) and o-terphenyl (O) contain the same number of carbon number but in different shapes—the former planar; the latter "propeller". The descriptor "retention factor ratio" between triphenylene (T) and o-terphenyl (O), $\alpha_{T/O}=k_T/k_O$, is a measure of the shape selectivity of the stationary phase, which is influenced by the spacing of the ligands and also the shape and functionality of the silylating reagent used to form the stationary phase. The terms $k_T$ and $k_O$ represent the capacity factor for the chemical species T and O, respectively. Stationary phases with a high shape selectivity more effectively resolve analytes with different shape. As shown in FIG. 14, after incorporation of a hydrophobic moiety into the bonded phase through the epoxy ring-opening reaction, steric selectivity of resulting bonded phases increase significantly.

Test condition: column, phases 14 and 21-24, 5-µm, 3×150-mm; mobile phase, methanol/water (80:20 v/v); flow rate, 0.425 mL/min; injection volume, 3 µL; temperature, 30° C.; detection, 254 nm; and test probes: o-terphenyl and triphenylene (0.1 mg/mL each).

Example 18B

Aqueous-Compatibility Test

The column packed with phase 23 was tested using an eluent of 10 mM ammonium acetate (pH5) at 30° C. A freshly packed column is washed with 10 column volumes of acetonitrile, and then equilibrated with 20 column volumes of mobile phase. The test standard contained cytosine, uracil and thymine. In the stop-flow experiment, each testing cycle consisted of two steps. Step one: the column was equilibrated with the mobile phase for 5 min, and the standard was injected for data acquisition. Step two: flow was stopped for 5 min before starting the next cycle.

Figure 15:
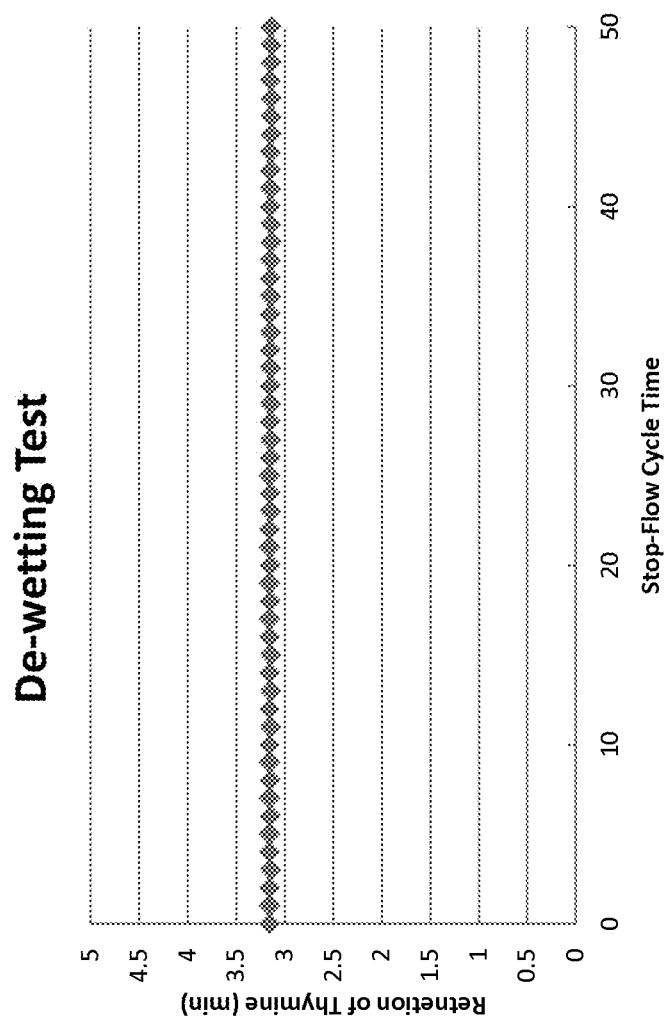
FIG. 15 shows that the RP media synthesized by epoxide ring-opening reaction (Phase 23) is fully compatible with highly aqueous conditions—no retention loss was observed during stop-flow test. The chromatogram was acquired under the following conditions: Column, Phase 23, 3 μm; Dimensions, 3.0×150 mm; Mobile Phase, 10 mM ammonium acetate, pH5; Temperature, 30° C.; Flow Rate, 0.425 mL/min; Inj. Volume, 3 μL; Detection, UV (254 nm); Sample, thymine (0.1 mg/mL); Stop-Flow Protocol, test the column under above condition, stop the pump for 5 min (pump pressure drops to 0), resume the flow and condition the column under above condition for 5 min, inject the sample and run the test under the same conditions. Repeat 2 through 4.

Many reverse phase columns are not compatible with highly aqueous mobile phase due to "de-wetting" as the result of high surface coverage of silica particles with hydrophobic alkyl chains. Although low ligand density bonding is used to achieve better compatibility with 100% aqueous mobile phases, these phases are usually associated with low hydrolytic stability. Because the epoxy or hydroxyl bonded phases usually have high bonding density and the resulting phases by epoxy ring-opening reaction have both polar-embedded group and reversed-phase moiety, phase 23 performs consistently well under 100% aqueous conditions—no retention loss is observed (FIG. 15).

Test condition: column, phase 23, 5-µm, 3×150-mm; mobile phase, 10 mM ammonium acetate, pH5; flow rate, 0.425 mL/min; injection volume, 3 µL; temperature, 30° C.; detection, 254 nm; and test probe: Thymine (0.1 mg/mL each).

Example 19

Protein Separation by HIC

Figure 16:
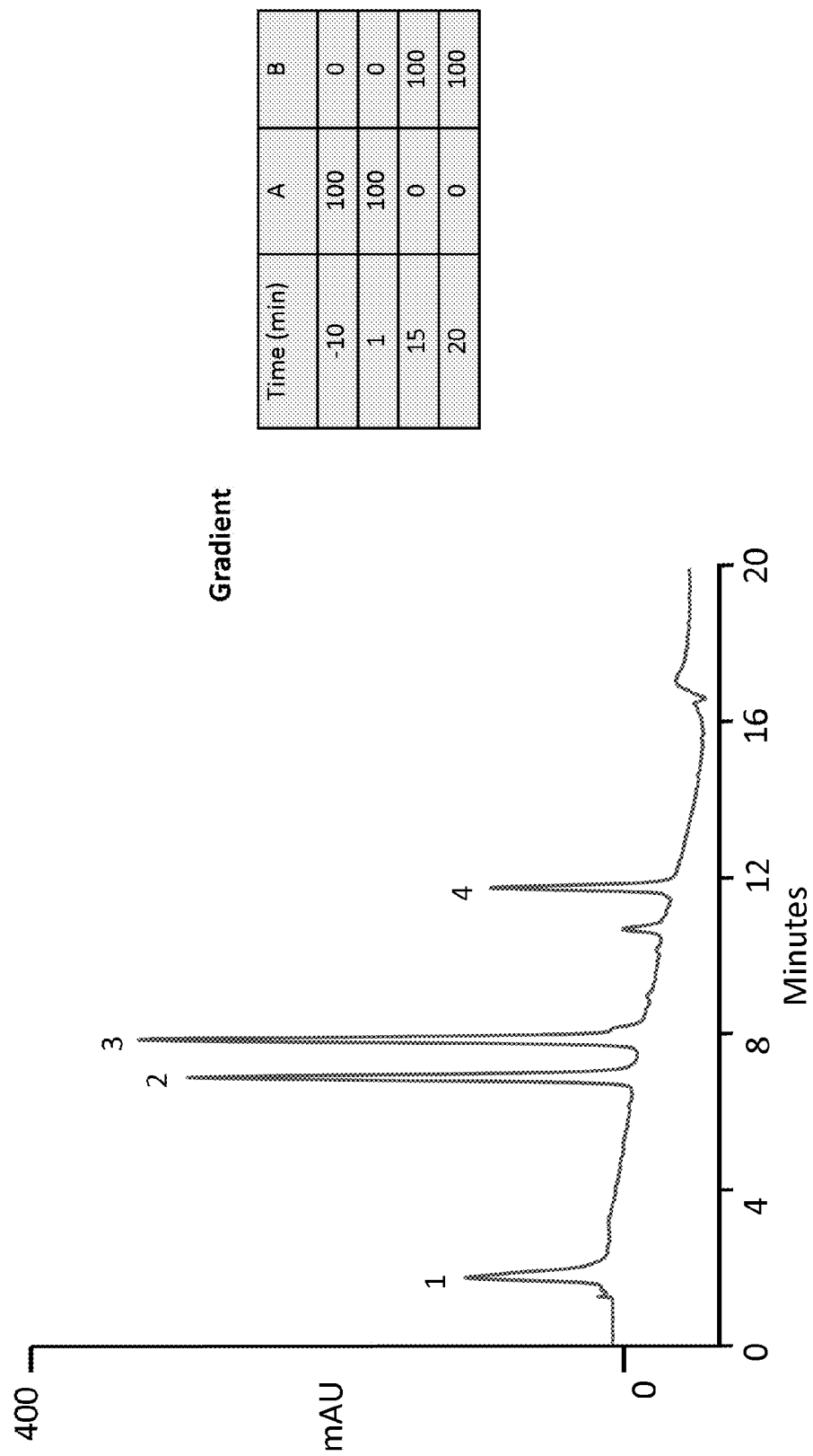
FIG. 16 shows that Phase 27 provides high resolution, high efficiency and excellent peak shape for proteins, each of which are desired features for a good HIC media: ideal selectivity; high resolution; high efficiency or sharp peak shape. The chromatogram was acquired under the following conditions: Column, Phase 27, 5 μm; Dimensions, 4.6×100 mm; Mobile Phase, A: 2 M $(NH_4)_2SO_4$ in 0.1M phosphate, pH7, and B, 0.1M phosphate, pH7; Temperature, 30° C.; Flow Rate, 1.0 mL/min; Inj. Volume, 5 μL; Detection, UV at 210 nm; Sample, (~0.5 mg/mL) containing, 1. Cytochrome C, 2. Ribonuclease A, 3. Lysozyme, and 4. α-Chymotrypsin.

A 4.6×100-mm column packed with Phase 27 was used to separate four proteins in the HIC condition. As shown in FIG. 16, this column provided high resolution, narrow peaks and excellent peak shape for all proteins, suggesting all desired features for a good HIC media.

Test condition: column, phase 27, 5-µm, 4.6×100-mm; mobile phase, A. 2 M $(NH_4)_2SO_4$ in 0.1M phosphate, pH 7 and B. 0.1 M phosphate, pH 7; flow rate, 1.0 mL/min; injection volume, 5 µL; temperature, 30° C.; detection, 210 nm. Sample (~0.5 mg/mL each): 1. Cytochrome C; 2. Ribonuclease A; 3. Lysozyme; 4. α-Chymotrypsin. The gradient condition is described below:

| Time (min) | % A | % B |
| --- | --- | --- |
| −10 | 100 | 0 |
| 0 | 100 | 0 |
| 1 | 100 | 0 |

| Time (min) | % A | % B |
| --- | --- | --- |
| 15 | 0 | 100 |
| 20 | 0 | 100 |

Example 20

Preparation of Ligand 1. To a stirred solution of 50 g 1,2-epoxy-9-decene (e.g., Aldrich), 100 g of $(MeO)_2MeSiH$ (e.g., Gelest) in 30 mL of toluene in a 1-L round bottom flask at ambient temperature were carefully added 0.5 g of Pt(0) catalyst (0.1% wt) (e.g., Gelest). Occasionally, an exothermic reaction is observed upon addition of the catalyst. The flask was equipped with a condenser and the reaction mixture was heated to 50° C. for 8 h. The reaction was monitored using gas chromatography. When the conversion was found to be higher than 60% by GC, all volatiles were removed in vacuo. Ligand 1 was obtained by Kugelrohr Distillation (140° C./0.11 torr).

Example 21

Figure 17:
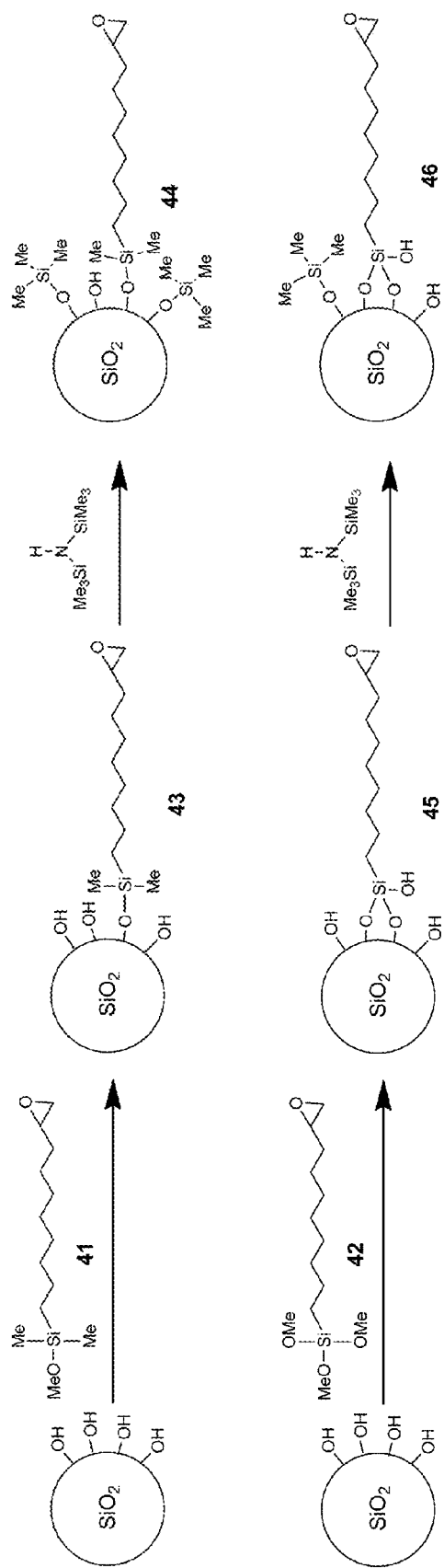
FIG. 17 illustrates the preparation of Phases 43-46.

Preparation of Ligand 41. To a stirred solution of 50 g of 1,2-epoxy-9-decene (e.g., Aldrich), 100 g of $(MeO)Me_2SiH$ (e.g., Gelest) in 30 mL of toluene in a 1-L round bottom flask at ambient temperature were carefully added 0.5 g of Pt(0) catalyst (0.1% wt) (e.g., Gelest). Occasionally, an exothermic reaction is observed upon addition of the catalyst. The flask was equipped with a condenser and the reaction mixture was heated to 50° C. for 8 h. The reaction was monitored using gas chromatography. When the conversion was found to be higher than 60% by GC, all volatiles were removed in vacuo. Ligand 41 was obtained by Kugelrohr Distillation (120° C./0.05 torr). FIG. 17.

Example 22

Preparation of Ligand 42. To a stirred solution of 50 g of 1,2-epoxy-9-decene (e.g., Aldrich), 100 g of $(MeO)_3SiH$ (e.g., Gelest) in 30 mL of toluene in a 1-L round bottom flask at ambient temperature were carefully added 0.5 g of Pt(0) catalyst (0.1% wt) (e.g., Gelest). Occasionally, an exothermic reaction is observed upon addition of the catalyst. The flask was equipped with a condenser and the reaction mixture was heated to 50° C. for 8 h. The reaction was monitored using gas chromatography. When the conversion was found to be higher than 60% by GC, all volatiles were removed in vacuo. Ligand 42 was obtained by Kugelrohr Distillation (160° C./0.05 torr). FIG. 17.

Example 23

Preparation of Phase 43 and Phase 44 (FIG. 17)

Weigh 20 g of dried porous spherical silica particles (particle size, 5-μm; pore size, 120-Å; surface area, 300 m$^2$/g) in a 250-mL round bottom flask. Then add a solution of silyl ligand 41 (20 g) in toluene (50 mL) to the flask. After carefully dispersing above slurry, the reaction mixture is put under stable refluxing and stirring for 48 hours. The functionalized silica particles are filtered and thoroughly washed with acetone to give Phase 43.

Phase 43 (10 g) in a 250-mL round bottom flask was combined with 20 g hexamethyldisilazane (e.g., Gelest) and toluene (50 mL). After carefully dispersing the slurry, the reaction mixture was maintained under stable reflux and stirring for 48 hours. The resulting silica particles were filtered and thoroughly washed with acetone, and finally dried under vacuum at 50° C. for 2 hours to give Phase 44.

Example 24

Preparation of Phase 45 and Phase 46 (FIG. 17)

Dried porous spherical silica particles (20 g, particle size, 5-μm; pore size, 120-Å; surface area, 300 m$^2$/g) can be combined in a 250-mL round bottom flask with a solution of silyl ligand 42 (20 g) in toluene (50 mL). After carefully dispersing the slurry, the reaction mixture can be put under stable refluxing and stirring for 48 hours. The functionalized silica particles can be filtered and thoroughly washed with acetone to give Phase 45.

Dried Phase 45 (10 g) in a 250-mL round bottom flask can be combined with 20 g hexamethyldisilazane (e.g., Gelest) and toluene (50 mL). After carefully dispersing the slurry, the reaction mixture can be maintained under stable reflux and stirring for 48 hours. The resulting silica particles can be filtered and thoroughly washed with acetone, and finally dried under vacuum at 50° C. for 2 hours to give Phase 46.

Example 25

Preparation of Phase 16

Phase 12 (10 g) can be dispersed into 100 mL of acetonitrile and D.I. water in 1:1 ratio. Glycero diglycidyl ether (5.0 g, Aldrich, Cat#: 475734, CAS[27043-36-3]) can be added to the mixture, which was mechanically stirred to uniformity. A base can be added to the resulting mixture to allow cross-linking between oxirane and hydroxyl groups to form a dense neutral hydrophilic layer that masks the surface silanol groups. Filtration of the reaction mixture and washing of the filter the cake with D.I. water (200 mL) and acetone (200 mL) can yield Phase 16. FIG. 11.

Example 26

Preparation of Phase 47

Dried porous spherical silica particles (20 g, particle size, 5-μm; pore size, 1000-Å; surface area, 25 m$^2$/g) in a 250-mL round bottom flask was combined with a solution of silyl ligand 2 (10 g) in toluene (50 mL). After carefully dispersing the slurry, the reaction mixture was maintained under stable reflux and stirring for 48 h. The resulting silica was filtered and thoroughly washed with acetone before being re-dispersed into 100 mL of acetonitrile and D.I. water in 1:1 ratio. Glycero glycidyl ether (5 g, e.g, Aldrich) was added to the mixture, which was followed mechanical stirring to uniformity. A base was added to the resulting mixture to allow cross-linking between oxirane and hydroxyl groups to form a dense neutral hydrophilic layer that masks the surface silanol groups. Filtering the reaction mixture and washing the cake with D.I. water (200 mL) and acetone (200 mL) gave Phase 47. It should be noted that Phase 47 is similar to Phase 16 except that the particles have a different pore size and surface area.

Example 27

Preparation of Phase 48

Dried Phase 47 (2.0 G) and 20 mL of toluene (anhydrous) were combined in a 40-mL glass vial with a septum cap. After sealing the vial with the cap, the slurry was mixed to uniformity. Propylene oxide (0.5 mL, Compound 7) was added through the septum with a syringe, and the slurry was mixed well. After cooling the mixture with ice-water bath down to ~4° C., boron trifluoride diethyl etherate (BF$_3$.Et$_2$O) (0.1 mL) was added through the septum with a syringe. The reaction mixture was maintained at ambient temperature with gentle mixing for 30 min. The reaction mixture was filtered followed by washing the filter cake with methanol (50 mL), D.I. water (50 mL) and acetone (100 mL) to give Phase 48. It should be noted that Phase 48 is similar to Phase 27 except that the particles have a different pore size and surface area.

Example 28

Preparation of Phase 49

Dried Phase 47 (2.0 g) and 20 mL of toluene (anhydrous) were combined in a 40-mL glass vial with a septum cap. After sealing the vial with the cap, the slurry was mixed to uniformity. 1,2-Butylene oxide (Compound 8) (0.5 mL) was added through the septum with a syringe, and the slurry was mixed well. After cooling the mixture with ice-water bath down to ~4° C., boron trifluoride diethyl etherate (BF$_3$.Et$_2$O) (0.1 mL) was added through the septum with a syringe. The reaction mixture was maintained at ambient temperature with gentle mixing for 30 min. The reaction mixture was filtered followed by washing the filter cake with methanol (50 mL), D.I. water (50 mL) and acetone (100 mL) to give Phase 49. It should be noted that Phase 49 is similar to Phase 30 except that the particles have a different pore size and surface area.

Example 29

Preparation of Phase 50

Figure 18:
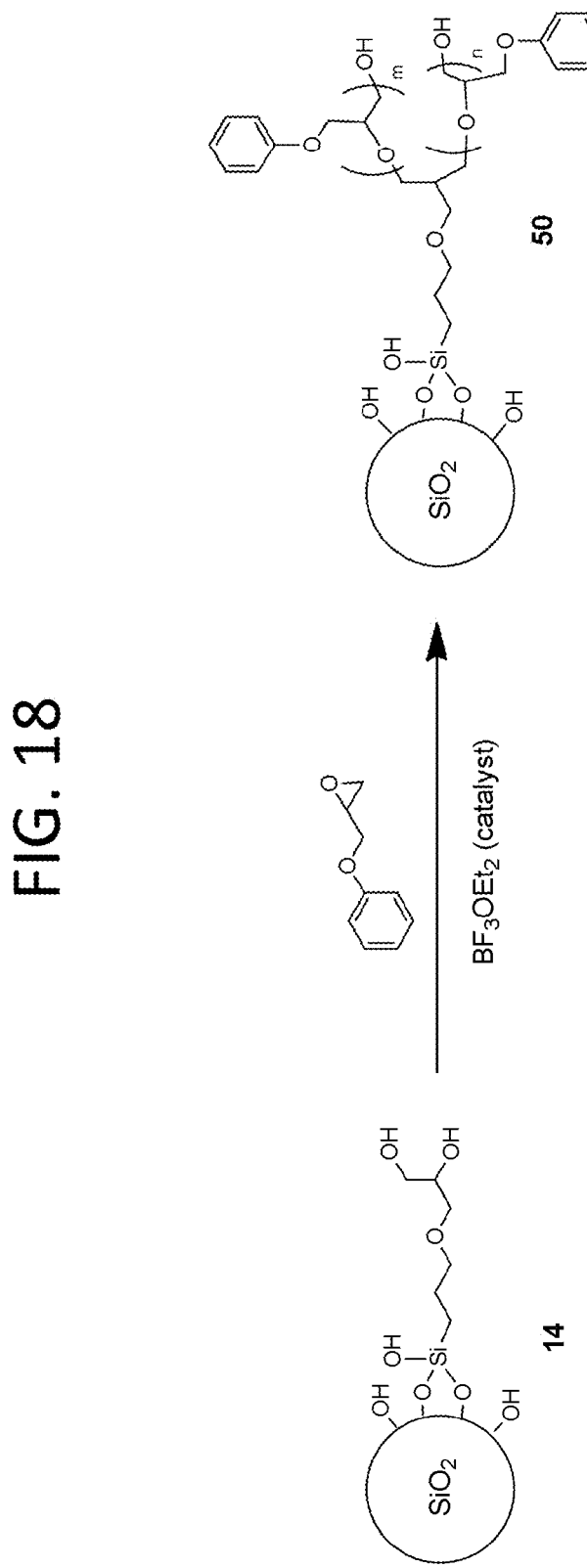
FIG. 18 illustrates the preparation of Phase 50.

Phase 14 (2.0 g, vacuum oven dried at 50° C. for 20 h) and 20 mL of toluene (anhydrous) can be combined in a 40 mL glass vial with a septum cap. After sealing the vial with the cap, the slurry can be mixed to uniformity. Phenyl glycidyl ether (e.g., Aldrich) (2.0 mL) can be added through the septum with a syringe, and the slurry can be mixed well. BF$_3$.Et$_2$O (0.1 mL) can be added through the septum with a syringe. The reaction mixture can be maintained at ambient temperature with gentle mixing for 30 min. The reaction mixture can be filtered followed by washing the filter cake with methanol (50 mL), D.I. water (50 mL) and acetone (100 mL) to give Phase 50. FIG. 18.

Example 30

Preparation of Phase 51

Figure 19:
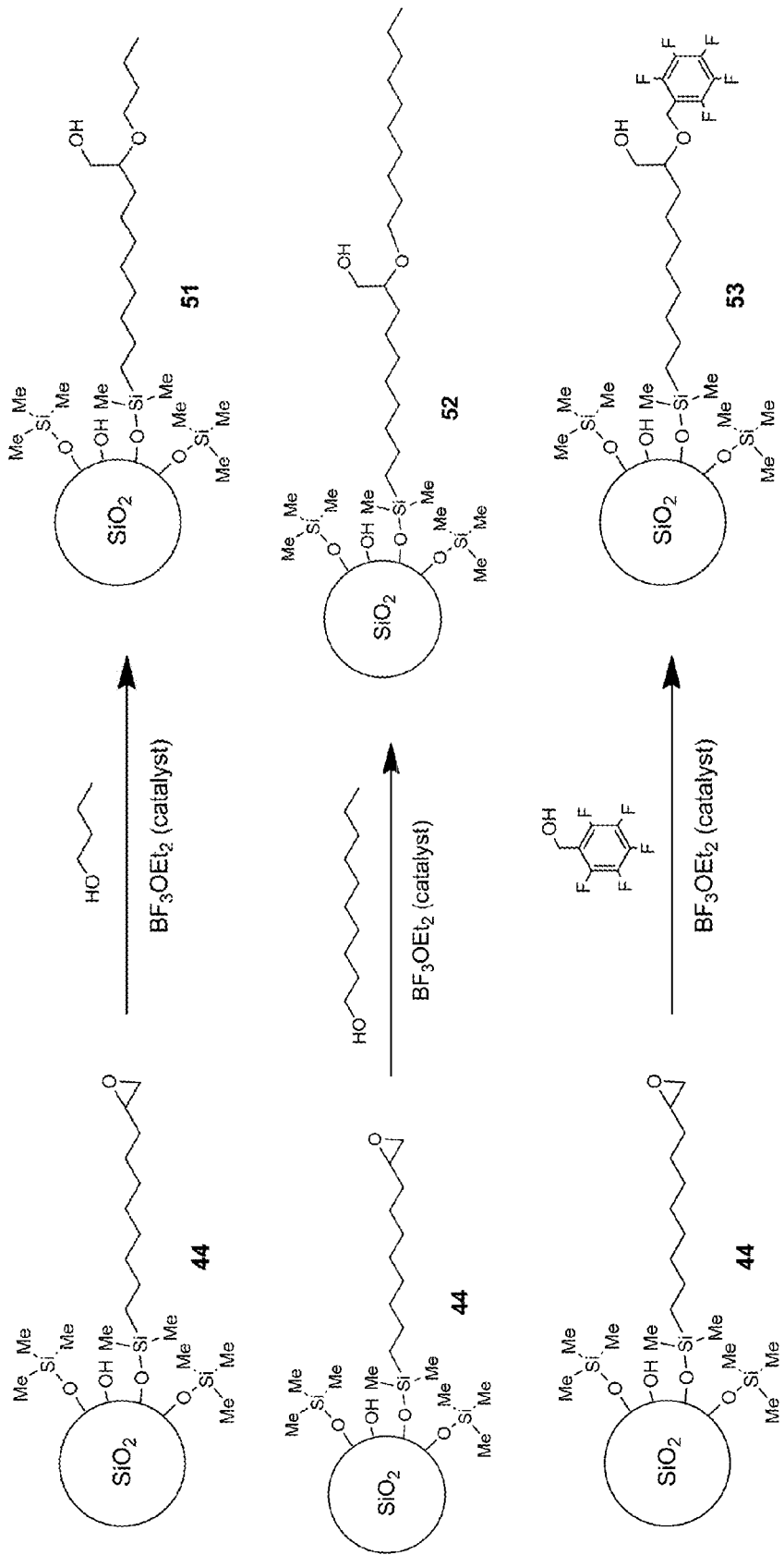
FIG. 19 illustrates the preparation of Phases 51-53.

Phase 44 (2.0 g, vacuum oven dried at 50° C. for 20 h) and 20 mL of toluene (anhydrous) were combined in a 40-mL glass vial with a septum cap. After sealing the vial with the cap, the slurry was mixed to uniformity. 1-Butanol (e.g., Aldrich) (2.0 mL) was added through the septum with a syringe, and the slurry as mixed well. BF$_3$.Et$_2$O (0.1 mL) was added through the septum with a syringe. The reaction mixture was maintained at ambient temperature with gentle mixing for 30 min. The reaction mixture was filtered followed by washing the filter cake with methanol (50 mL), D.I. water (50 mL) and acetone (100 mL) to give Phase 51. FIG. 19.

Example 31

Preparation of Phase 52

Phase 44 (2.0 g, vacuum oven dried at 50° C. for 20 h) and 20 mL of toluene (anhydrous) were combined in a 40-mL glass vial with a septum cap. After sealing the vial with the cap, the slurry was mixed to uniformity. 1-Decanol (e.g., Aldrich; 3.0 g) was added and the slurry was mixed well. BF$_3$.Et$_2$O (0.1 mL) was added through the septum with a syringe. The reaction mixture was maintained at ambient temperature with gentle mixing for 30 min. The reaction mixture was filtered followed by washing the filter cake with methanol (50 mL), D.I. water (50 mL) and acetone (100 mL) to give Phase 52. FIG. 19.

Example 32

Preparation of Phase 53

Phase 44 (2.0 g, vacuum oven dried at 50° C. for 20 h) and 20 mL of toluene (anhydrous) can be combined in a 40-mL glass vial with a septum cap. After sealing the vial with the cap, the slurry can be mixed to uniformity. 2,3,4,5,6-Pentafluorobenzyl alcohol (e.g., Aldrich) (3 mL) can be added and the slurry can be mixed well. BF$_3$.Et$_2$O (0.1 mL) can be added through the septum with a syringe. The reaction mixture can be maintained at ambient temperature with gentle mixing for 30 min. The reaction mixture can be filtered followed by washing the filter cake with methanol (50 mL), D.I. water (50 mL) and acetone (100 mL) to give Phase 53. FIG. 19.

Example 33

Preparation of Phase 54

Figure 20:
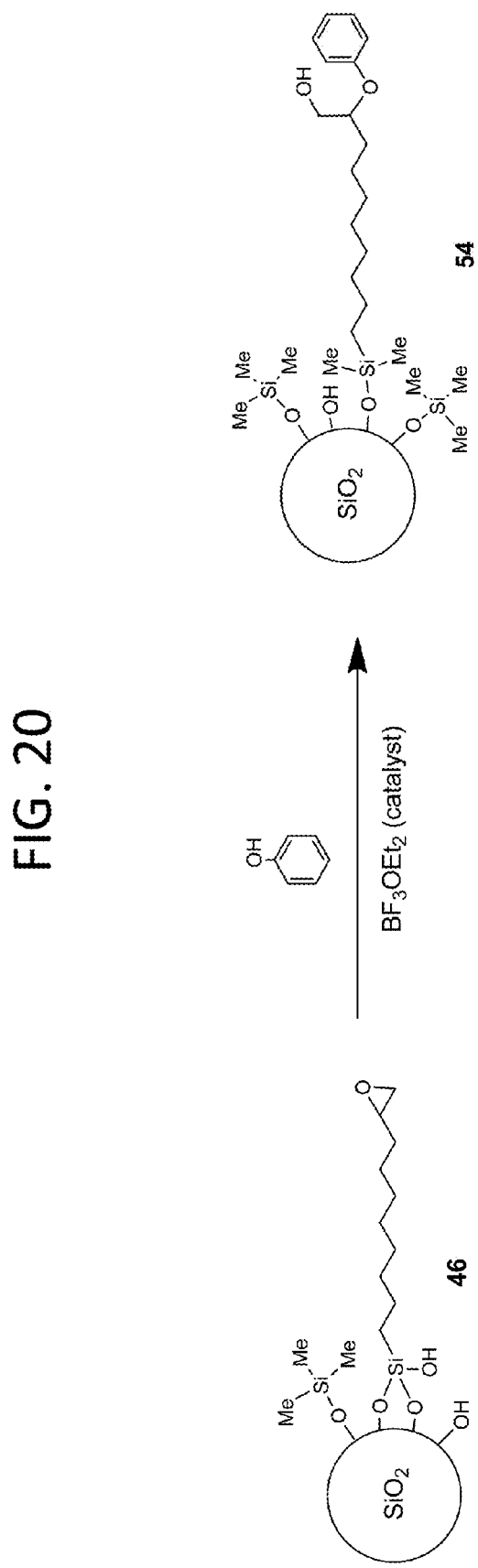
FIG. 20 illustrates the preparation of Phase 54.

Phase 46 (2.0 g, vacuum oven dried at 50° C. for 20 h) and 20 mL of toluene (anhydrous) can be combined in a 40-mL glass vial with a septum cap. After sealing the vial with the cap, the slurry can be mixed to uniformity. Phenol (e.g., Aldrich; 2.0 g) can be added and the slurry was well mixed. BF$_3$.Et$_2$O (0.1 mL) can be added through the septum with a syringe. The reaction mixture can be maintained at ambient temperature with gentle mixing for 30 min. The reaction mixture can be filtered followed by washing the filter cake with methanol (50 mL), D.I. water (50 mL) and acetone (100 mL) to give Phase 54. FIG. 20.

Example 34

Preparation of Phase 55

Figure 21:
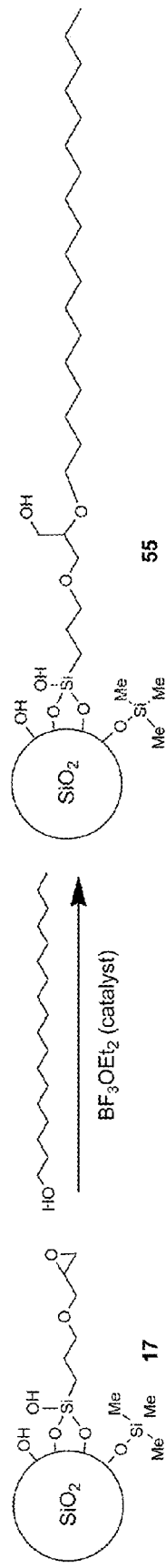
FIG. 21 illustrates the preparation of Phase 55.

Phase 17 (2.0 g, vacuum oven dried at 50° C. for 20 h) and 20 mL of toluene (anhydrous) were combined in a 40-mL glass vial with a septum cap. After sealing the vial with the cap, the slurry was mixed to uniformity. 1-Octadecanol (e.g., Aldrich; 4.0 g) was added and the slurry well was well mixed. BF$_3$.Et$_2$O (0.1 mL) was added through the septum with a syringe. Keep the reaction mixture at ambient temperature with gentle mixing for 30 min. The reaction mixture was filtered followed by washing the cake with methanol (50 mL), D.I. water (50 mL) and acetone (100 mL) to give Phase 55. FIG. 21.

It is understood that the examples and embodiments described herein are for illustrative purposes only and that various modifications or changes in light thereof will be suggested to persons skilled in the art and are to be included within the spirit and purview of this application and scope of the appended claims. It is to be understood that the present invention covers all combinations of aspects and/or embodiments, as well as suitable, convenient and preferred groups described herein. All publications, patents, and patent applications cited herein are hereby incorporated by reference in their entirety for all purposes.

What is claimed is:

1. A composition comprising a ligand covalently bound to a substrate, said ligand having a structure according to Formula (I)

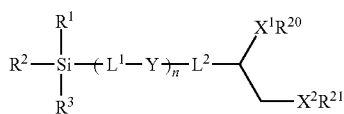

wherein
n is an integer selected from 0 and 1;
$X^1$ is O or S;
$X^2$ is O or S,
with the proviso that at least one of $X^1$ or $X^2$ is O;
$R^{20}$ is selected from the group consisting of, substituted or unsubstituted phenyl, and linear or branched alkyl optionally substituted with hydroxyl or alkoxy substituted with hydroxy;
$R^{21}$ is selected from the group consisting of H, substituted or unsubstituted phenyl, and linear or branched alkyl optionally substituted with hydroxy or alkoxy substituted with hydroxy;
$R^1$, $R^2$ and $R^3$ are independently selected from the group consisting of halogen, $OR^{10}$, $NR^{10}R^{11}$, $OC(O)R^{12}$, $OS(O)_2R^{12}$, substituted or unsubstituted alkyl, substituted or unsubstituted heteroalkyl, substituted or unsubstituted aryl, substituted or unsubstituted heteroaryl, substituted or unsubstituted heterocycloalkyl and a bond to said substrate
wherein
each $R^{10}$ and each $R^{11}$ is selected independently from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl and a bond to a silica gel substrate;
each $R^{12}$ is independently selected from the group consisting of substituted or unsubstituted alkyl, substituted or unsubstituted heteroalkyl, substituted or unsubstituted aryl, substituted or unsubstituted heteroaryl, and substituted or unsubstituted heterocycloalkyl,
with the proviso that at least one of $R^1$, $R^2$ and $R^3$ is covalently bound to said substrate, and
with the proviso that at least one of $R^1$, $R^2$ and $R^3$ is unsubstituted $C_1$-$C_3$ alkyl or OH;
$L^1$ and $L^2$ are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl;
and Y is O.

2. The composition of claim 1, wherein $R^1$, $R^2$ and $R^3$ are selected independently from the group consisting of $OR^{10}$, $OC(O)R^{12}$,
$OS(O)_2R^{12}$, unsubstituted alkyl and a bond to said substrate, wherein
each $R^{10}$ and each $R^{11}$ is selected independently from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl and a bond to said substrate;
each $R^{12}$ is selected independently from the group consisting of substituted or unsubstituted alkyl, substituted or unsubstituted heteroalkyl, substituted or unsubstituted aryl, substituted or unsubstituted heteroaryl, and substituted or unsubstituted heterocycloalkyl;

$L^1$ is $C_3$ unsubstituted alkyl; and
$L^2$ is $C_1$-$C_8$ unsubstituted alkyl.

3. The composition of claim 1, wherein
$R^{20}$ is selected from the group consisting of substituted or unsubstituted phenyl, unsubstituted linear or branched alkyl, and alkyl substituted with substituted or unsubstituted phenyl;
$R^{21}$ is selected from the group consisting of H, substituted or unsubstituted phenyl, unsubstituted linear or branched alkyl, and alkyl substituted with substituted or unsubstituted phenyl;
$R^1$, $R^2$ and $R^3$ are selected independently from the group consisting of $OR^{10}$, $OC(O)R^{12}$, $OS(O)_2R^{12}$, and unsubstituted alkyl,
wherein
each $R^{10}$ and each $R^{11}$ is selected independently from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl and a bond to said silica gel substrate;
each $R^{12}$ is selected independently from the group consisting of substituted or unsubstituted alkyl, substituted or unsubstituted heteroalkyl, substituted or unsubstituted aryl, substituted or unsubstituted heteroaryl, and substituted or unsubstituted heterocycloalkyl;
$L^1$ and $L^2$ are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl; and
Y is O.

4. The composition of claim 1, wherein $R^{21}$ is selected from the group consisting of unsubstituted $C_1$-$C_{10}$ alkyl, methyl substituted with substituted or unsubstituted phenyl, and substituted or unsubstituted phenyl.

5. The composition of claim 3, wherein $X^2R^{21}$ is OH.

6. The composition of claim 5, wherein $R^{20}$ is selected from the group consisting of unsubstituted $C_1$-$C_{10}$ alkyl, methyl substituted with substituted or unsubstituted phenyl, and substituted or unsubstituted phenyl.

7. The composition of claim 6, wherein $R^{20}$ is selected from the group consisting of methyl, ethyl, unsubstituted $C_4$ alkyl, unsubstituted $C_{10}$ alkyl, methyl substituted with halogen-substituted phenyl, and unsubstituted phenyl.

8. The composition of claim 1, wherein the compound has a structure according to Formula (II)

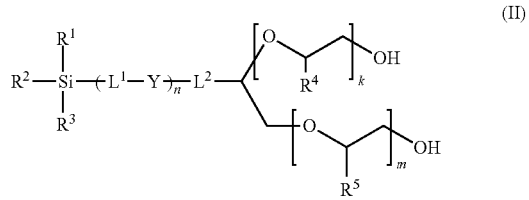

wherein
n is an integer selected from 0 and 1;
(k+m) is an integer from 1 to 20;
$R^4$ is unsubstituted $C_1$-$C_{10}$ alkyl or phenyl; and
$R^5$ is unsubstituted $C_1$-$C_{10}$ alkyl or phenyl.

9. The composition of claim 8, wherein the compound has a structure according to Formula (II)

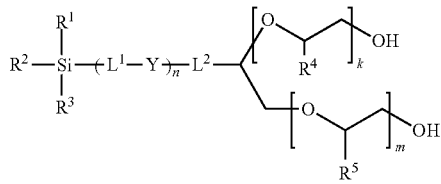

(II)

in which
n is an integer selected from 0 and 1;
(k+m) is an integer from 1 to 20;
$R^4$ is methyl, ethyl, hexadecyl or phenyl; and
$R^5$ is methyl, ethyl, hexadecyl or phenyl.

10. The composition of claim 8, wherein
k is 0 and m is 1; or
k is 1 and m is 0; or
k is 1 and m is 1; or
k is 0 and m is 2; or
k is 2 and m is 0.

11. The composition of claim 1, wherein at least two of $R^1$, $R^2$ and $R^3$ are bonds to said substrate.

12. The composition of claim 1, wherein $R^1$ and $R^2$ are bonds to said substrate, and $R^3$ is unsubstituted $C_1$-$C_3$ alkyl or OH.

13. The composition of claim 1, wherein $R^1$ and $R^2$ are bonds to said substrate, and $R^3$ is methyl.

14. The composition of claim 1, wherein $R^1$ and $R^2$ are bonds to said substrate, and $R^3$ is OH.

15. The composition of claim 1, wherein n is 0, and $L^2$ is $C_1$-$C_8$ unsubstituted alkyl.

16. The composition of claim 1, wherein n is 0, and $L^2$ is $C_5$-$C_8$ unsubstituted alkyl.

17. The composition of claim 1, wherein n is 0, and $L^2$ is $C_8$ unsubstituted alkyl.

18. The composition of claim 1, wherein n is 1, and $L^1$ is $C_2$-$C_5$ unsubstituted alkyl, and $L^2$ is $C_1$-$C_3$ unsubstituted alkyl.

19. The composition of claim 1, wherein n is 1, and $L^1$ is $C_3$ unsubstituted alkyl, and $L^2$ is $C_1$ unsubstituted alkyl.

20. The composition of claim 1, comprising a cross-link in the ligand according to Formula I, formed by reaction of a hydroxyl moiety and an epoxide moiety wherein at least one of said hydroxyl moiety and said epoxide moiety are pendent from the ligand according to Formula I of said composition, said cross-linked formed by a method comprising:
   (a) contacting a substrate with a first ligand comprising a first epoxide moiety under conditions appropriate for binding the first ligand to the substrate;
   (b) contacting the product of step (a) with a bifunctional reagent having at least one hydroxyl moiety and at least a second epoxide moiety under basic conditions, thereby forming a cross-link by reacting said hydroxyl moiety with a member selected from the first epoxide moiety, the second epoxide moiety and a combination thereof; and optionally,
   (c) contacting the product of step (b) with an epoxide reagent under conditions appropriate to react said epoxide reagent with a hydroxyl moiety on the product of step (b).

21. The composition of claim 20, wherein step (b) is performed in the presence of a base.

22. The composition of claim 20, wherein said bifunctional reagent is glycerol diglycidyl ether.

23. The composition of claim 20, wherein step (c) is performed in the presence of $BF_3$-$Et_2O$.

24. A chromatographic system comprising the composition of claim 1 in a chromatographic column in fluidic communication with one or more of:
   a) a suppressor;
   b) an injection valve;
   c) a source of eluent; and
   d) a detector.

* * * * *